United States Patent
Taft et al.

(10) Patent No.: US 9,131,597 B2
(45) Date of Patent: Sep. 8, 2015

(54) ELECTROSURGICAL SYSTEM AND METHOD FOR TREATING HARD BODY TISSUE

(75) Inventors: Richard J. Taft, Austin, TX (US); Danielle Seybold, Santa Clara, CA (US)

(73) Assignee: ArthroCare Corporation, Austin, TX (US)

( * ) Notice: Subject to any disclaimer, the term of this patent is extended or adjusted under 35 U.S.C. 154(b) by 1207 days.

(21) Appl. No.: 13/019,654

(22) Filed: Feb. 2, 2011

(65) Prior Publication Data

US 2012/0197344 A1  Aug. 2, 2012

(51) Int. Cl.
*A61B 18/14* (2006.01)
*H05H 1/46* (2006.01)
*A61B 18/00* (2006.01)
*A61N 1/32* (2006.01)
*A61N 1/44* (2006.01)

(52) U.S. Cl.
CPC .............. *H05H 1/46* (2013.01); *A61B 18/148* (2013.01); *A61B 2018/00565* (2013.01); *A61B 2018/00577* (2013.01); *A61B 2018/00583* (2013.01); *A61B 2018/00589* (2013.01); *A61B 2018/144* (2013.01); *A61B 2018/1407* (2013.01); *A61B 2018/1425* (2013.01); *A61B 2018/1472* (2013.01); *A61B 2218/007* (2013.01); *A61N 1/326* (2013.01); *A61N 1/44* (2013.01); *H05H 2001/466* (2013.01); *H05H 2245/122* (2013.01)

(58) Field of Classification Search
USPC .......................................... 606/41, 45–50, 79
See application file for complete search history.

(56) References Cited

U.S. PATENT DOCUMENTS

| | | | |
|---|---|---|---|
| 2,050,904 A | 4/1936 | Trice | 219/31 |
| 2,056,377 A | 10/1939 | Wappler | 125/303 |
| 2,611,365 A | 9/1952 | Rubens | 606/42 |
| 3,434,476 A | 3/1969 | Shaw et al. | 606/22 |
| 3,633,425 A | 1/1972 | Sanford | 73/356 |
| 3,707,149 A | 12/1972 | Hao et al. | 128/303.14 |
| 3,718,617 A | 2/1973 | Royal | 260/30.4 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |

(Continued)

FOREIGN PATENT DOCUMENTS

| | | | | |
|---|---|---|---|---|
| DE | 3119735 | | 1/1983 | A61B 17/39 |
| DE | 3930451 A1 | | 3/1991 | A61B 17/39 |

(Continued)

OTHER PUBLICATIONS

PCT Notification of the International Search Report and Written Opinion for PCT/US2011/033784 11 pgs, Mailed Jul. 18, 2011.

(Continued)

*Primary Examiner* — Michael Peffley
(74) *Attorney, Agent, or Firm* — Norman F. Hainer, Jr.

(57) ABSTRACT

A method of preparing a target hard body tissue, such as osseous or dental tissue, to receive an implant component including; positioning an active electrode in proximity to a target tissue and proximate an electrically conductive fluid, followed by applying a high frequency voltage between the active electrode and a return electrode, the high frequency voltage sufficient to form a plasma. This plasma modifies at least a portion of the target tissue. An implant component may then be placed adjacent at least a portion of the modified target tissue.

70 Claims, 21 Drawing Sheets

(56) References Cited

U.S. PATENT DOCUMENTS

| | | | | |
|---|---|---|---|---|
| 3,939,839 A | 2/1976 | Curtiss | | 128/303 |
| 3,963,030 A | 6/1976 | Newton | | 606/40 |
| 3,964,487 A | 6/1976 | Judson | | 606/39 |
| 3,970,088 A | 7/1976 | Morrison | | 128/303 |
| 4,033,351 A | 7/1977 | Hetzel | | 606/48 |
| 4,040,426 A | 8/1977 | Morrison, Jr. | | 128/303 |
| 4,043,342 A | 8/1977 | Morrison, Jr. | | 128/303 |
| 4,074,718 A | 2/1978 | Morrison, Jr. | | 128/303 |
| 4,092,986 A | 6/1978 | Schneiderman | | 128/303 |
| D249,549 S | 9/1978 | Pike | | D24/144 |
| 4,114,623 A | 9/1978 | Meinke et al. | | 606/39 |
| 4,116,198 A | 9/1978 | Roos | | 128/303 |
| 4,181,131 A | 1/1980 | Ogiu | | 128/303 |
| 4,184,492 A | 1/1980 | Meinke et al. | | 128/303 |
| 4,202,337 A | 5/1980 | Hren et al. | | 128/303 |
| 4,228,800 A | 10/1980 | Degler, Jr. et al. | | 128/303 |
| 4,232,676 A | 11/1980 | Herczog | | 128/303 |
| 4,240,441 A | 12/1980 | Khalil | | 600/505 |
| 4,248,231 A | 2/1981 | Herczog et al. | | 128/303 |
| 4,301,801 A | 11/1981 | Schneiderman | | 606/38 |
| 4,326,529 A | 4/1982 | Doss et al. | | 128/303 |
| 4,346,715 A | 8/1982 | Gammell | | 607/99 |
| 4,363,324 A | 12/1982 | Kusserow | | 607/64 |
| 4,378,801 A | 4/1983 | Oosten | | 606/37 |
| 4,381,007 A | 4/1983 | Doss | | 128/303 |
| 4,418,692 A | 12/1983 | Guay | | 606/42 |
| 4,474,179 A | 10/1984 | Koch | | 606/40 |
| 4,476,862 A | 10/1984 | Pao | | 128/303 |
| 4,509,532 A | 4/1985 | DeVries | | 128/736 |
| 4,520,818 A | 6/1985 | Mickiewicz | | 606/40 |
| 4,532,924 A | 8/1985 | Auth et al. | | 128/303 |
| 4,548,207 A | 10/1985 | Reimels | | 128/303 |
| 4,567,890 A | 2/1986 | Ohta et al. | | 128/303 |
| 4,572,206 A | 2/1986 | Geddes et al. | | 600/505 |
| 4,580,557 A | 4/1986 | Hertzmann | | 606/12 |
| 4,587,975 A | 5/1986 | Salo et al. | | 600/506 |
| 4,590,934 A | 5/1986 | Malis et al. | | 128/303 |
| 4,593,691 A | 6/1986 | Lindstrom et al. | | 128/303 |
| 4,658,817 A | 4/1987 | Hardy | | 606/14 |
| 4,660,571 A | 4/1987 | Hess et al. | | 128/784 |
| 4,674,499 A | 6/1987 | Pao | | 128/303 |
| 4,682,596 A | 7/1987 | Bales et al. | | 128/303 |
| 4,706,667 A | 11/1987 | Roos | | 128/303 |
| 4,709,698 A | 12/1987 | Johnston et al. | | 606/41 |
| 4,727,874 A | 3/1988 | Bowers et al. | | 128/303 |
| 4,750,902 A | 6/1988 | Wuchinich et al. | | 604/22 |
| 4,765,331 A | 8/1988 | Petruzzi et al. | | 128/303 |
| 4,785,823 A | 11/1988 | Eggers et al. | | 128/692 |
| 4,805,616 A | 2/1989 | Pao | | 128/303 |
| 4,823,791 A | 4/1989 | D'Amelio et al. | | 123/303 |
| 4,832,048 A | 5/1989 | Cohen | | 128/786 |
| 4,846,179 A | 7/1989 | O'Connor | | 607/72 |
| 4,860,752 A | 8/1989 | Turner | | 607/102 |
| 4,898,169 A | 2/1990 | Norman et al. | | 606/42 |
| 4,907,589 A | 3/1990 | Cosman | | 606/34 |
| 4,920,978 A | 5/1990 | Colvin | | 128/784 |
| 4,931,047 A | 6/1990 | Broadwin et al. | | 604/22 |
| 4,936,281 A | 6/1990 | Stasz | | 128/660 |
| 4,936,301 A | 6/1990 | Rexroth et al. | | 606/45 |
| 4,943,290 A | 7/1990 | Rexroth et al. | | 606/45 |
| 4,955,377 A | 9/1990 | Lennox et al. | | 607/105 |
| 4,966,597 A | 10/1990 | Cosman | | 606/50 |
| 4,967,765 A | 11/1990 | Turner et al. | | 128/785 |
| 4,976,711 A | 12/1990 | Parins et al. | | 606/48 |
| 4,979,948 A | 12/1990 | Geddes et al. | | 606/33 |
| 4,998,933 A | 3/1991 | Eggers et al. | | 606/41 |
| 5,007,908 A | 4/1991 | Rydell | | 606/47 |
| 5,009,656 A | 4/1991 | Reimels | | 606/48 |
| 5,026,387 A | 6/1991 | Thomas | | 606/169 |
| 5,035,696 A | 7/1991 | Rydell | | 606/47 |
| 5,047,026 A | 9/1991 | Rydell | | 606/48 |
| 5,047,027 A | 9/1991 | Rydell | | 606/48 |
| 5,057,105 A | 10/1991 | Malone et al. | | 606/28 |
| 5,057,106 A | 10/1991 | Kasevich et al. | | 606/33 |
| 5,078,717 A | 1/1992 | Parins et al. | | 606/48 |
| 5,080,660 A | 1/1992 | Buelna | | 606/45 |
| 5,083,565 A | 1/1992 | Parins et al. | | 600/374 |
| 5,084,044 A | 1/1992 | Quint | | 606/27 |
| 5,085,659 A | 2/1992 | Rydell | | 606/47 |
| 5,086,401 A * | 2/1992 | Glassman et al. | | 700/259 |
| 5,088,997 A | 2/1992 | Delahuerga et al. | | 606/42 |
| 5,092,339 A | 3/1992 | Geddes et al. | | 606/505 |
| 5,098,431 A | 3/1992 | Rydell | | 606/48 |
| 5,099,840 A | 3/1992 | Goble | | 128/422 |
| 5,102,410 A | 4/1992 | Dressel | | 606/15 |
| 5,108,391 A | 4/1992 | Flachenecker et al. | | 606/38 |
| RE33,925 E | 5/1992 | Bales et al. | | 606/48 |
| 5,112,330 A | 5/1992 | Nishigaki et al. | | 606/46 |
| 5,122,138 A | 6/1992 | Manwaring | | 606/46 |
| 5,125,928 A | 6/1992 | Parins et al. | | 606/48 |
| 5,156,151 A | 10/1992 | Imran | | 600/375 |
| 5,167,659 A | 12/1992 | Ohtomo et al. | | 606/40 |
| 5,171,311 A | 12/1992 | Rydell et al. | | 606/48 |
| 5,174,304 A | 12/1992 | Latina et al. | | 607/141 |
| 5,178,620 A | 1/1993 | Eggers et al. | | 606/41 |
| 5,183,338 A | 2/1993 | Wickersheim et al. | | 374/131 |
| 5,190,517 A | 3/1993 | Zieve et al. | | 604/22 |
| 5,192,280 A | 3/1993 | Parins | | 606/48 |
| 5,195,959 A | 3/1993 | Smith | | 604/34 |
| 5,197,466 A | 3/1993 | Marchosky et al. | | 128/399 |
| 5,197,963 A | 3/1993 | Parins | | 606/46 |
| 5,207,675 A | 5/1993 | Canady | | 606/40 |
| 5,217,457 A | 6/1993 | Delahuerga et al. | | 606/42 |
| 5,217,459 A | 6/1993 | Kamerling | | 606/48 |
| 5,249,585 A | 10/1993 | Turner et al. | | 607/99 |
| 5,255,980 A | 10/1993 | Thomas et al. | | 374/161 |
| 5,261,410 A | 11/1993 | Alfano et al. | | 600/475 |
| 5,267,994 A | 12/1993 | Gentelia et al. | | 606/15 |
| 5,267,997 A | 12/1993 | Farin et al. | | 606/38 |
| 5,273,524 A | 12/1993 | Fox et al. | | 604/21 |
| 5,277,201 A | 1/1994 | Stern | | 607/98 |
| 5,281,216 A | 1/1994 | Klicek | | 606/42 |
| 5,281,218 A | 1/1994 | Imran | | 606/41 |
| 5,282,799 A | 2/1994 | Rydell | | 606/48 |
| 5,290,282 A | 3/1994 | Casscells | | 606/29 |
| 5,300,069 A | 4/1994 | Hunsberger et al. | | 606/37 |
| 5,306,238 A | 4/1994 | Fleenor | | 606/42 |
| 5,312,400 A | 5/1994 | Bales et al. | | 606/41 |
| 5,314,406 A | 5/1994 | Arias et al. | | 604/21 |
| 5,318,563 A | 6/1994 | Malis et al. | | 606/38 |
| 5,324,254 A | 6/1994 | Phillips | | 604/21 |
| 5,330,470 A | 7/1994 | Hagen | | 606/42 |
| 5,334,140 A | 8/1994 | Philips | | 604/35 |
| 5,334,183 A | 8/1994 | Wuchinich | | 606/46 |
| 5,334,193 A | 8/1994 | Nardella | | 606/41 |
| 5,336,172 A | 8/1994 | Bales et al. | | 604/27 |
| 5,336,220 A | 8/1994 | Ryan et al. | | 604/22 |
| 5,336,443 A | 8/1994 | Odashima | | 252/511 |
| 5,342,357 A | 8/1994 | Nardella | | 606/40 |
| 5,348,026 A * | 9/1994 | Davidson | | 128/898 |
| 5,348,554 A | 9/1994 | Imran et al. | | 606/41 |
| 5,354,291 A | 10/1994 | Bales et al. | | 604/35 |
| 5,366,443 A | 11/1994 | Eggers et al. | | 604/114 |
| 5,370,675 A | 12/1994 | Edwards et al. | | 607/101 |
| 5,374,261 A | 12/1994 | Yoon | | 604/385.01 |
| 5,375,588 A | 12/1994 | Yoon | | 128/4 |
| 5,380,277 A | 1/1995 | Phillips | | 604/33 |
| 5,380,316 A | 1/1995 | Aita et al. | | 606/7 |
| 5,383,874 E | 1/1995 | Jackson et al. | | 606/1 |
| 5,383,876 A | 1/1995 | Nardella | | 606/49 |
| 5,383,917 A | 1/1995 | Desai et al. | | 607/702 |
| 5,389,096 A | 2/1995 | Aita | | 606/15 |
| 5,395,312 A | 3/1995 | Desai | | 604/22 |
| 5,400,267 A | 3/1995 | Denen et al. | | 702/59 |
| 5,401,272 A | 3/1995 | Perkins | | 606/15 |
| 5,403,311 A | 4/1995 | Abele et al. | | 606/49 |
| 5,417,687 A | 5/1995 | Nardella et al. | | 606/32 |
| 5,419,767 A | 5/1995 | Eggers et al. | | 604/114 |
| 5,423,810 A | 6/1995 | Goble et al. | | 606/40 |
| 5,423,882 A | 6/1995 | Jackman et al. | | 607/122 |
| 5,436,566 A | 7/1995 | Thompson et al. | | 324/713 |
| 5,437,662 A | 8/1995 | Nardella | | 606/40 |
| 5,438,302 A | 8/1995 | Goble | | 331/167 |
| 5,441,499 A | 8/1995 | Fritzsch | | 606/45 |

(56) References Cited

U.S. PATENT DOCUMENTS

| | | | |
|---|---|---|---|
| 5,449,356 A | 9/1995 | Walbrink et al. | 606/49 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,458,597 A | 10/1995 | Edwards et al. | 606/41 |
| 5,472,443 A | 12/1995 | Cordis et al. | 606/48 |
| 5,472,444 A * | 12/1995 | Huebner et al. | 606/64 |
| 5,486,161 A | 1/1996 | Lax et al. | 604/22 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,730 A | 4/1996 | Edwards | 606/41 |
| 5,507,743 A | 4/1996 | Edwards et al. | 606/41 |
| 5,514,130 A | 5/1996 | Baker | 606/41 |
| 5,540,683 A | 7/1996 | Ichikawa et al. | 606/40 |
| 5,542,915 A | 8/1996 | Edwards et al. | 604/22 |
| 5,549,598 A | 8/1996 | O'Donnell, Jr. | 606/6 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,573,533 A | 11/1996 | Strul | 606/34 |
| 5,584,872 A | 12/1996 | LaFontaine et al. | 607/117 |
| 5,588,960 A | 12/1996 | Edwards et al. | 604/20 |
| 5,599,350 A | 2/1997 | Schulze et al. | 606/51 |
| 5,609,151 A | 3/1997 | Mulier et al. | 128/642 |
| 5,609,573 A | 3/1997 | Sandock | 604/22 |
| 5,633,578 A | 5/1997 | Eggers et al. | 323/301 |
| 5,634,921 A | 6/1997 | Hood et al. | 606/5 |
| 5,643,304 A | 7/1997 | Schechter et al. | 606/171 |
| 5,647,869 A | 7/1997 | Goble et al. | 606/37 |
| 5,658,278 A | 8/1997 | Imran et al. | 606/41 |
| 5,660,567 A | 8/1997 | Nierlich et al. | 439/620.21 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,697,925 A | 12/1997 | Taylor | 606/34 |
| 5,697,927 A | 12/1997 | Imran et al. | 606/41 |
| 5,700,262 A | 12/1997 | Acosta et al. | |
| 5,715,817 A | 2/1998 | Stevens-Wright et al. | 600/373 |
| 5,722,975 A | 3/1998 | Edwards et al. | 606/41 |
| 5,725,524 A | 3/1998 | Mulier et al. | 606/41 |
| 5,749,869 A | 5/1998 | Lindenmeier et al. | 606/34 |
| 5,749,871 A | 5/1998 | Hood et al. | 606/50 |
| 5,749,914 A | 5/1998 | Janssen | 607/116 |
| 5,755,753 A | 5/1998 | Knowlton | 607/98 |
| 5,766,153 A | 6/1998 | Eggers et al. | 604/114 |
| 5,769,847 A | 6/1998 | Panescu et al. | 606/42 |
| 5,785,705 A | 7/1998 | Baker | 606/32 |
| 5,786,578 A | 7/1998 | Christy et al. | 219/720 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,836,897 A | 11/1998 | Sakurai et al. | 601/2 |
| 5,843,019 A | 12/1998 | Eggers et al. | 604/22 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,873,877 A | 2/1999 | McGaffigan et al. | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,944,715 A * | 8/1999 | Goble et al. | 606/41 |
| 5,954,716 A | 9/1999 | Sharkey et al. | 606/32 |
| 5,964,786 A | 10/1999 | Ochs et al. | 607/5 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,066,489 A | 5/2000 | Fields et al. | 435/236 |
| 6,068,628 A | 5/2000 | Fanton et al. | 606/41 |
| 6,074,386 A | 6/2000 | Goble et al. | 606/34 |
| 6,086,585 A | 7/2000 | Hovda et al. | 606/45 |
| 6,090,106 A | 7/2000 | Goble et al. | 606/41 |
| 6,090,107 A | 7/2000 | Borgmeier et al. | 606/41 |
| 6,093,186 A | 7/2000 | Goble et al. | 606/34 |
| 6,102,046 A * | 8/2000 | Weinstein et al. | 128/898 |
| 6,103,298 A | 8/2000 | Edelson et al. | 427/77 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,135,999 A | 10/2000 | Fanton et al. | 606/45 |
| 6,142,992 A | 11/2000 | Cheng et al. | 606/34 |
| 6,149,620 A | 11/2000 | Baker et al. | 604/22 |
| 6,156,334 A | 12/2000 | Meyer-ingold et al. | 424/443 |
| 6,159,194 A | 12/2000 | Eggers et al. | 604/500 |
| 6,159,208 A | 12/2000 | Hovda et al. | 606/41 |
| 6,162,217 A | 12/2000 | Kannenberg et al. | 606/34 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,197,021 B1 | 3/2001 | Panescu et al. | 606/31 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,217,574 B1 | 4/2001 | Webster | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 606/32 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,238,393 B1 | 5/2001 | Mulier et al. | 606/41 |
| 6,241,723 B1 | 6/2001 | Heim et al. | 606/34 |
| 6,249,706 B1 | 6/2001 | Sobota et al. | 607/115 |
| 6,254,600 B1 | 7/2001 | Willink et al. | 606/41 |
| 6,258,087 B1 | 7/2001 | Edwards et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 604/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Ruhr et al. | 600/338 |
| 6,309,387 B1 | 10/2001 | Eggers et al. | 606/41 |
| 6,312,408 B1 | 11/2001 | Eggers et al. | 604/114 |
| 6,319,007 B1 | 11/2001 | Livaditis | 433/224 |
| 6,322,549 B1 | 11/2001 | Eggers et al. | 604/500 |
| 6,346,104 B2 | 2/2002 | Daly et al. | 606/34 |
| 6,346,107 B1 | 2/2002 | Cucin | 606/49 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,350 B1 | 4/2002 | Sharkey et al. | 606/41 |

(56) References Cited

U.S. PATENT DOCUMENTS

| | | | |
|---|---|---|---|
| 6,379,351 B1 | 4/2002 | Thapliyal et al. | 606/41 |
| 6,391,025 B1 | 5/2002 | Weinstein et al. | 606/41 |
| 6,409,722 B1 | 6/2002 | Hoey et al. | 606/34 |
| 6,416,507 B1 | 7/2002 | Eggers et al. | 606/41 |
| 6,416,508 B1 | 7/2002 | Eggers et al. | 606/32 |
| 6,416,509 B1 | 7/2002 | Goble et al. | 606/37 |
| 6,425,912 B1 | 7/2002 | Knowlton | 607/101 |
| 6,432,103 B1 | 8/2002 | Ellsberry et al. | 606/41 |
| 6,440,129 B1 | 8/2002 | Simpson | 606/42 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,500,173 B2 | 12/2002 | Underwood et al. | 606/32 |
| 6,514,248 B1 | 2/2003 | Eggers et al. | 606/41 |
| 6,514,250 B1 | 2/2003 | Jahns et al. | 606/41 |
| 6,517,498 B1 | 2/2003 | Burbank et al. | 600/564 |
| 6,530,922 B2 | 3/2003 | Cosman | 606/34 |
| 6,558,382 B2 | 5/2003 | Jahns et al. | 606/41 |
| 6,565,560 B1 | 5/2003 | Goble et al. | 606/41 |
| 6,578,579 B2 | 6/2003 | Burnside | 128/897 |
| 6,589,237 B2 * | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,635,034 B1 | 10/2003 | Cosmescu | 604/289 |
| 6,640,128 B2 | 10/2003 | Vilsmeier et al. | 600/427 |
| 6,656,177 B2 | 12/2003 | Truckai et al. | 606/51 |
| 6,663,554 B2 | 12/2003 | Babaev | 600/2 |
| 6,663,627 B2 | 12/2003 | Francischelli et al. | 606/41 |
| 6,702,810 B2 | 3/2004 | McClurken et al. | 606/34 |
| 6,730,080 B2 | 5/2004 | Harano et al. | 606/38 |
| 6,746,447 B2 | 6/2004 | Davison et al. | 606/41 |
| 6,749,604 B1 | 6/2004 | Eggers et al. | 606/41 |
| 6,749,608 B2 | 6/2004 | Garito et al. | 606/45 |
| D493,530 S | 7/2004 | Reschke | D24/144 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,780,184 B2 | 8/2004 | Tanrisever | 606/45 |
| 6,802,842 B2 | 10/2004 | Ellman et al. | 606/45 |
| 6,805,130 B2 * | 10/2004 | Tasto et al. | 128/898 |
| 6,830,558 B2 | 12/2004 | Flaherty et al. | 604/67 |
| 6,837,887 B2 | 1/2005 | Woloszko et al. | 606/41 |
| 6,837,888 B2 | 1/2005 | Ciarrocca et al. | 606/41 |
| 6,855,143 B2 | 2/2005 | Davison et al. | 606/41 |
| 6,864,686 B2 | 3/2005 | Novak et al. | 324/419 |
| 6,866,671 B2 | 3/2005 | Tierney et al. | 606/130 |
| 6,872,183 B2 | 3/2005 | Sampson et al. | 600/561 |
| 6,878,149 B2 | 4/2005 | Gatto | 606/46 |
| 6,890,307 B2 | 5/2005 | Kokate et al. | 600/549 |
| 6,892,086 B2 | 5/2005 | Russell | 600/372 |
| 6,911,027 B1 | 6/2005 | Edwards et al. | 606/40 |
| 6,920,883 B2 | 7/2005 | Bessette et al. | 128/898 |
| 6,921,398 B2 | 7/2005 | Carmel et al. | 606/41 |
| 6,929,640 B1 | 8/2005 | Underwood et al. | 606/32 |
| 6,949,096 B2 | 9/2005 | Davison et al. | 606/41 |
| 6,953,461 B2 | 10/2005 | McClurken et al. | 606/51 |
| 6,960,204 B2 | 11/2005 | Eggers et al. | 606/32 |
| 6,974,453 B2 | 12/2005 | Woloszko et al. | 606/41 |
| 6,979,328 B2 | 12/2005 | Baerveldt et al. | 606/6 |
| 6,979,601 B2 | 12/2005 | Marr et al. | 438/132 |
| 6,984,231 B2 | 1/2006 | Goble et al. | 606/37 |
| 6,986,770 B2 | 1/2006 | Hood | 606/41 |
| 6,991,631 B2 | 1/2006 | Woloszko et al. | 606/41 |
| 7,001,382 B2 | 2/2006 | Gallo | 606/41 |
| 7,004,941 B2 | 2/2006 | Tvinnereim et al. | 606/41 |
| 7,010,353 B2 | 3/2006 | Gan et al. | 607/50 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,094,231 B1 | 8/2006 | Ellman et al. | 606/37 |
| 7,104,986 B2 | 9/2006 | Hovda et al. | 606/32 |
| 7,115,139 B2 | 10/2006 | McClurken et al. | 607/96 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,223,265 B2 | 5/2007 | Keppel | 606/41 |
| 7,241,293 B2 | 7/2007 | Davison | 600/410 |
| 7,247,155 B2 | 7/2007 | Hoey et al. | 606/34 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,271,363 B2 | 9/2007 | Lee et al. | 219/121.43 |
| 7,276,061 B2 | 10/2007 | Schaer et al. | 607/41 |
| 7,276,063 B2 | 10/2007 | Davison et al. | 606/45 |
| 7,278,994 B2 | 10/2007 | Goble | 606/41 |
| 7,282,048 B2 | 10/2007 | Goble et al. | 606/34 |
| 7,297,143 B2 | 11/2007 | Ormsby et al. | 606/41 |
| 7,297,145 B2 | 11/2007 | Woloszko et al. | 606/41 |
| 7,318,823 B2 | 1/2008 | Sharps et al. | 606/32 |
| 7,331,956 B2 | 2/2008 | Hovda et al. | 606/32 |
| 7,335,199 B2 | 2/2008 | Goble et al. | 606/41 |
| RE40,156 E | 3/2008 | Sharps et al. | 606/32 |
| 7,344,532 B2 | 3/2008 | Goble et al. | 606/34 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,527,624 B2 | 5/2009 | Dubnack et al. | 606/41 |
| 7,572,251 B1 | 8/2009 | Davison et al. | 604/500 |
| 7,632,267 B2 | 12/2009 | Dahla | 606/41 |
| 7,678,069 B1 | 3/2010 | Baker et al. | 604/22 |
| 7,691,101 B2 | 4/2010 | Davison et al. | 606/41 |
| 7,699,830 B2 | 4/2010 | Martin | 604/540 |
| 7,704,249 B2 | 4/2010 | Woloszko et al. | 606/48 |
| 7,708,733 B2 | 5/2010 | Sanders et al. | 606/41 |
| 7,722,601 B2 | 5/2010 | Wham et al. | 606/34 |
| 7,785,322 B2 | 8/2010 | Penny et al. | 606/34 |
| 7,824,398 B2 | 11/2010 | Woloszko et al. | 606/32 |
| 7,862,560 B2 | 1/2011 | Marion | 606/34 |
| 7,879,034 B2 | 2/2011 | Woloszko et al. | 606/48 |
| 7,887,538 B2 * | 2/2011 | Bleich et al. | 606/79 |
| 7,892,230 B2 | 2/2011 | Woloszko et al. | 606/41 |
| 7,985,072 B2 | 7/2011 | Belikov et al. | 433/215 |
| D658,760 S | 5/2012 | Cox et al. | D24/144 |
| 8,192,424 B2 | 6/2012 | Woloszko | 606/40 |
| 8,303,583 B2 | 11/2012 | Hosier et al. | 606/48 |
| 8,568,405 B2 | 10/2013 | Cox et al. | 606/41 |
| 8,574,187 B2 | 11/2013 | Marion | 606/37 |
| 8,685,018 B2 | 4/2014 | Cox et al. | 606/41 |
| 8,747,399 B2 | 6/2014 | Woloszko et al. | 606/34 |
| 2002/0029036 A1 | 3/2002 | Goble et al. | 606/38 |
| 2002/0042612 A1 | 4/2002 | Hood et al. | 606/50 |
| 2002/0151882 A1 | 10/2002 | Marko et al. | 606/28 |
| 2002/0183739 A1 | 12/2002 | Long | 606/41 |
| 2003/0013986 A1 | 1/2003 | Saadat | 600/549 |
| 2003/0014045 A1 | 1/2003 | Russell | 606/41 |
| 2003/0014047 A1 | 1/2003 | Woloszko et al. | 606/41 |
| 2003/0088245 A1 | 5/2003 | Woloszko et al. | 606/41 |
| 2003/0158545 A1 | 8/2003 | Hovda et al. | 606/32 |
| 2003/0167035 A1 | 9/2003 | Flaherty et al. | 604/67 |
| 2003/0171743 A1 | 9/2003 | Tasto et al. | 606/32 |
| 2003/0181903 A1 | 9/2003 | Hood et al. | 606/49 |
| 2003/0208196 A1 | 11/2003 | Stone | 606/41 |
| 2003/0212396 A1 | 11/2003 | Eggers et al. | 606/41 |
| 2003/0216725 A1 | 11/2003 | Woloszko et al. | 606/41 |
| 2003/0216726 A1 | 11/2003 | Eggers et al. | 606/41 |
| 2003/0216732 A1 | 11/2003 | Truckai et al. | 606/49 |
| 2003/0232048 A1 | 12/2003 | Yang et al. | 424/141.1 |

(56) References Cited

U.S. PATENT DOCUMENTS

| | | | |
|---|---|---|---|
| 2004/0030330 A1 | 2/2004 | Brassell et al. | 606/41 |
| 2004/0058153 A1 | 3/2004 | Ren et al. | 428/408 |
| 2004/0092925 A1* | 5/2004 | Rizoiu et al. | 606/33 |
| 2004/0102044 A1 | 5/2004 | Mao et al. | 438/689 |
| 2004/0116922 A1 | 6/2004 | Hovda et al. | 606/41 |
| 2004/0127893 A1 | 7/2004 | Hovda | 606/41 |
| 2004/0186418 A1 | 9/2004 | Karashima | 604/20 |
| 2004/0230190 A1 | 11/2004 | Dahla et al. | 604/41 |
| 2005/0004634 A1 | 1/2005 | Hovda et al. | 606/41 |
| 2005/0010205 A1 | 1/2005 | Hovda et al. | 606/41 |
| 2005/0033278 A1 | 2/2005 | McClurken et al. | 606/34 |
| 2005/0197657 A1 | 9/2005 | Goth et al. | 606/41 |
| 2005/0245923 A1 | 11/2005 | Christopherson et al. | 606/41 |
| 2005/0261754 A1 | 11/2005 | Woloszko et al. | 606/32 |
| 2005/0273091 A1 | 12/2005 | Booth et al. | 607/99 |
| 2006/0036237 A1 | 2/2006 | Davison et al. | 606/41 |
| 2006/0095031 A1 | 5/2006 | Ormsby | 606/34 |
| 2006/0097615 A1 | 5/2006 | Tsakalakos et al. | 313/309 |
| 2006/0161148 A1 | 7/2006 | Behnke | 606/34 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0179495 A1 | 8/2007 | Mitchell et al. | 606/41 |
| 2007/0208335 A1 | 9/2007 | Woloszko et al. | 606/41 |
| 2007/0282323 A1 | 12/2007 | Woloszko et al. | 606/41 |
| 2008/0004615 A1* | 1/2008 | Woloszko et al. | 606/32 |
| 2008/0004621 A1 | 1/2008 | Dahla et al. | 606/48 |
| 2008/0077128 A1 | 3/2008 | Woloszko et al. | 606/41 |
| 2008/0138761 A1 | 6/2008 | Pond | 433/29 |
| 2008/0140069 A1 | 6/2008 | Filloux et al. | 606/41 |
| 2008/0154255 A1 | 6/2008 | Panos et al. | 606/33 |
| 2008/0167645 A1 | 7/2008 | Woloszko | 606/40 |
| 2008/0234674 A1 | 9/2008 | McClurken et al. | 606/50 |
| 2008/0243116 A1 | 10/2008 | Anderson | 606/41 |
| 2008/0261368 A1 | 10/2008 | Ramin et al. | 438/287 |
| 2008/0300590 A1 | 12/2008 | Horne et al. | 606/35 |
| 2009/0209956 A1 | 8/2009 | Marion | 606/34 |
| 2009/0222001 A1 | 9/2009 | Greeley | 606/33 |
| 2010/0042101 A1 | 2/2010 | Inagaki et al. | 606/52 |
| 2010/0121317 A1 | 5/2010 | Lorang et al. | 606/41 |
| 2010/0152726 A1 | 6/2010 | Cadouri et al. | 606/41 |
| 2010/0228246 A1 | 9/2010 | Marion | 606/37 |
| 2010/0292689 A1 | 11/2010 | Davison et al. | 606/41 |
| 2010/0318083 A1 | 12/2010 | Davison et al. | 606/41 |
| 2010/0324549 A1 | 12/2010 | Marion | 606/37 |
| 2010/0331883 A1* | 12/2010 | Schmitz et al. | 606/249 |
| 2011/0137308 A1 | 6/2011 | Woloszko et al. | 606/41 |
| 2011/0208177 A1 | 8/2011 | Brannan | 606/33 |
| 2011/0245826 A1 | 10/2011 | Woloszko et al. | 606/41 |
| 2011/0270256 A1* | 11/2011 | Nelson et al. | 606/85 |
| 2011/0319887 A1 | 12/2011 | Keppel | 606/41 |
| 2012/0083782 A1 | 4/2012 | Stalder et al. | 606/41 |
| 2012/0095453 A1 | 4/2012 | Cox et al. | 606/33 |
| 2012/0095454 A1 | 4/2012 | Cox et al. | 606/33 |
| 2012/0109123 A1 | 5/2012 | Woloszko et al. | 606/45 |
| 2012/0196251 A1 | 8/2012 | Taft et al. | 433/216 |
| 2012/0215221 A1 | 8/2012 | Woloszko | 606/50 |
| 2012/0296328 A1 | 11/2012 | Marion | 606/34 |
| 2013/0116680 A1 | 5/2013 | Woloszko | 606/33 |
| 2014/0018798 A1 | 1/2014 | Cox et al. | 606/41 |
| 2014/0025065 A1 | 1/2014 | Marion | 606/33 |
| 2014/0135760 A1 | 5/2014 | Cadouri et al. | 606/41 |
| 2014/0155882 A1 | 6/2014 | Cox et al. | 606/34 |
| 2014/0236141 A1 | 8/2014 | Woloszko et al. | 606/34 |
| 2014/0257277 A1 | 9/2014 | Woloszko et al. | 606/41 |
| 2014/0257278 A1 | 9/2014 | Woloszko et al. | 606/41 |
| 2014/0257279 A1 | 9/2014 | Woloszko et al. | 606/41 |
| 2014/0276725 A1 | 9/2014 | Cox | 606/33 |
| 2015/0032101 A1 | 1/2015 | Woloszko et al. | 606/40 |

FOREIGN PATENT DOCUMENTS

| | | | |
|---|---|---|---|
| DE | 69635311 T2 | 4/2007 | A61B 18/12 |
| DE | 10201003288 | 9/2014 | A61B 18/12 |
| EP | 423757 | 3/1996 | A61B 17/39 |
| EP | 0703461 A2 | 3/1996 | G01B 27/02 |
| EP | 0740926 A2 | 11/1996 | A61B 17/39 |
| EP | 0754437 A2 | 1/1997 | A61B 17/39 |
| EP | 0694290 B1 | 11/2000 | A61B 18/04 |
| EP | 1334699 | 8/2003 | A61B 18/12 |
| EP | 1428480 | 6/2004 | A61B 18/12 |
| EP | 1707147 | 10/2006 | A61B 18/12 |
| FR | 2313949 | 1/1977 | A61N 3/02 |
| GB | 467502 | 6/1937 | |
| GB | 2160102 | 12/1985 | A61B 17/38 |
| GB | 2299216 | 9/1996 | H01F 30/12 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| GB | 2333455 | 7/1999 | G01K 11/12 |
| GB | 2406793 | 4/2005 | A61B 18/00 |
| GB | 2514442 | 11/2014 | A61B 18/14 |
| JP | 57-57802 | 4/1982 | A61B 1/00 |
| JP | 57-117843 | 7/1982 | A61B 17/39 |
| WO | 90/03152 | 4/1990 | A61B 17/39 |
| WO | 90/07303 | 7/1990 | A61B 17/39 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/04220 | 3/1994 | |
| WO | 94/08654 | 4/1994 | A61M 37/00 |
| WO | 94/10921 | 5/1994 | A61B 18/00 |
| WO | 94/26228 | 11/1994 | A61B 18/14 |
| WO | 95/34259 | 12/1995 | A61F 5/48 |
| WO | 96/00040 | 1/1996 | A61B 18/00 |
| WO | 96/00042 | 1/1996 | A61B 17/39 |
| WO | 96/39086 | 12/1996 | A61B 18/12 |
| WO | 97/00646 | 1/1997 | A61B 17/39 |
| WO | 97/00647 | 1/1997 | A61B 17/39 |
| WO | 97/18768 | 5/1997 | A61B 17/39 |
| WO | 97/24073 | 7/1997 | A61B 17/39 |
| WO | 97/24074 | 7/1997 | A61B 17/39 |
| WO | 97/24993 | 7/1997 | A61B 17/39 |
| WO | 97/24994 | 7/1997 | A61B 17/39 |
| WO | 97/43971 | 11/1997 | A61B 17/39 |
| WO | 97/48345 | 12/1997 | A61B 17/39 |
| WO | 97/48346 | 12/1997 | A61B 17/39 |
| WO | 98/07468 | 2/1998 | A61N 1/40 |
| WO | 98/26724 | 6/1998 | A61B 17/36 |
| WO | 98/27879 | 7/1998 | A61B 17/36 |
| WO | 98/27880 | 7/1998 | A61B 17/39 |
| WO | 98/56324 | 12/1998 | A61F 7/12 |
| WO | 99/20213 | 4/1999 | A61F 7/12 |
| WO | 99/51155 | 10/1999 | A61B 17/39 |
| WO | 99/51158 | 10/1999 | A61B 17/39 |
| WO | 99/56648 | 11/1999 | A61B 17/39 |
| WO | 00/00098 | 1/2000 | A61B 17/36 |
| WO | 00/09053 | 2/2000 | A61F 7/12 |
| WO | 00/62685 | 10/2000 | A61B 17/20 |
| WO | 01/24720 | 4/2001 | A61B 18/18 |
| WO | 01/87154 | 5/2001 | A61B 5/05 |
| WO | 01/95819 | 12/2001 | A61B 18/14 |
| WO | 02/36028 | 5/2002 | A61B 18/12 |
| WO | 02/102255 | 12/2002 | A61B 17/20 |
| WO | 03/024305 | 3/2003 | |
| WO | 03/092477 | 11/2003 | |
| WO | 2004/026150 | 4/2004 | A61B 17/22 |
| WO | 2004/071278 | 8/2004 | |
| WO | 2005/125287 | 12/2005 | A61B 18/00 |
| WO | 2007/006000 | 1/2007 | A61B 18/14 |
| WO | 2007/056729 | 5/2007 | A61B 18/14 |
| WO | 2010/052717 | 5/2010 | A61B 18/14 |

(56) References Cited

FOREIGN PATENT DOCUMENTS

| | | | | |
|---|---|---|---|---|
| WO | 2012/050636 | 4/2012 | ............ | A61B 18/14 |
| WO | 2012/050637 | 4/2012 | ............ | A61B 18/14 |

OTHER PUBLICATIONS

PCT Notification of the International Search Report and Written Opinion for PCT/US2011/033761 11 pgs, Mailed Jul. 22, 2011.
UK Search Report for GB1110342.1 3pgs, Oct. 18, 2011.
Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.
BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual" , 15 pgs, Jul. 1991.
Cook et al., "Therapeutic Medical Devices: Application and Design" , Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artherosclerotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of Escherichia Coli by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of Excherichia Coli and Streptococcus Mutans", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

(56) References Cited

OTHER PUBLICATIONS

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, Clinica, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Buchelt, et al. "Excimer Laser Ablation of Fibrocartilage: An In Vitro and In Vivo Study", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
Rand et al., "Effect of Elecctrocautery on Fresh Human Articular Cartilage", J. Arthro. Surg., vol. 1, pp. 242-246, 1985.
European Examination Report for EP 02773432 4 pgs, Sep. 22, 2009.
European Examination Report for EP 05024974 4 pgs, Dec. 5, 2008.
European Examination Report for EP 04708664 7pgs, Sep. 7, 2009.
European Examination Report for EP 02749601.7 4pgs, Dec. 2, 2009.
European Examination Report 2 for EP 04708664 5pgs, May 3, 2010.
European Search Report for EP 02773432 3pgs, Dec. 19, 2008.
European Search Report for EP 04708664.0 5pgs, Apr. 6, 2009.
European Search Report for EP 98953859, 2 pgs, Jul. 2, 2001.
Suppl European Search Report for EP 98953859, 3 pgs, Oct. 18, 2001.
Extended European Search Report for EP09152846, 8pgs, Jan. 5, 2010.
European Search Report for EP 99945039.8, 3 pgs, Oct. 1, 2001.
European Search Report for EP 09152850, 2 pgs, Dec. 29, 2009.
PCT International Preliminary Examination Report for PCT/US02/19261, 3pgs, Mar. 25, 2003.
PCT International Search Report for PCT/US02/19261, 1 pg, Mailed Sep. 18, 2002.
PCT International Search Report for PCT/US02/29476, 1 pg, Mailed May 24, 2004.
PCT International Search Report for PCT/US03/13686, 1 pg, Mailed Nov. 25, 2003.
PCT International Search Report for PCT/US04/03614, 1 pg, Mailed Sep. 14, 2004.
PCT International Search Report for PCT/US98/22323, 1 pg, Mailed Mar. 3, 1999.
PCT International Search Report for PCT/US99/14685, 1 pg, Mailed Oct. 21, 1999.
PCT International Search Report for PCT/US99/18289, 1 pg, Mailed Dec. 7, 1999.
PCT Notification of International Preliminary Examination Report for PCT/US98/22323, 5 pgs, Mailed Nov. 28, 2000.
PCT Notification of International Preliminary Examination Report for PCT/US99/14685, 4 pgs, Mailed Feb. 20, 2001.
PCT Notification of International Preliminary Examination Report for PCT/US99/18289, 4 pgs, Mailed Jul. 7, 2000.
PCT Notification of International Search Report and Written Opinion for PCT/US06/26321, 8pgs, Mailed Apr. 25, 2007.
PCT Notification of the International Search Report and Written Opinion for PCT/US06/60618, 7pgs, Mailed Oct. 5, 2007.
PCT Notification of the International Search Report and Written Opinion for PCT/US07/69856, 7pgs, Mailed Jun. 5, 2008.
PCT Written Opinion of the International Searching Authority for PCT/US04/03614, 4 pgs, Mailed Sep. 14, 2004.
UK Search Report for GB0800129.9 2pgs, May 8, 2008.
UK Search Report for GB0805062.7 1 pg, Jul. 16, 2008.
UK Search Report for GB0900604.0 4 pgs, May 15, 2009.
Slager et al., "Electrical nerve and Muscle Stimulation by Radio Frequency Surgery: Role of Direct Current Loops Around the Active Electrode", IEEE Transactions on Biomedical engineering, vol. 40, No. 2, pp. 182-187, Feb. 1993.
European Examination Report (3rd) for EP 04708664 6pgs, Nov. 6, 2012.
UK Suppl Search Report for GB1110342.1 2pgs, Aug. 16, 2012.
UK Combined Search and Exam Report for GB1403997.8 5pgs, Sep. 17, 2014.
Elgrabli, D., Abella-Gallart, S., Aguerre-Chariol, O., Robidel F.R., Boczkowski, J., Lacroix, G. (2007). Effect of BSA on carbon nanotube dispersion in vivi and in vitro studies. vol. 1, No. 4, pp. 266-278, 2007.
"Work functions for photoelectric effect". (2001). Retrieved on Jun. 11, 2014 from http://hyperphysics.phyastr.gsu.edu/hbase/tables/photoelec.html, 2001.
Jing et al. (2007). Biocompatibility of Cerium Oxide Films Synthesized by Dual Plasma Deposition. Key Enginerring Materials. vol. 330-332.pp. 749-752, 2007.
Wikipedia Field Electron Emission. Retrieved on Dec. 29, 2014 from http://en.wikipedia.org/wiki/Field_electron_emission, Dec. 29, 2014.

\* cited by examiner

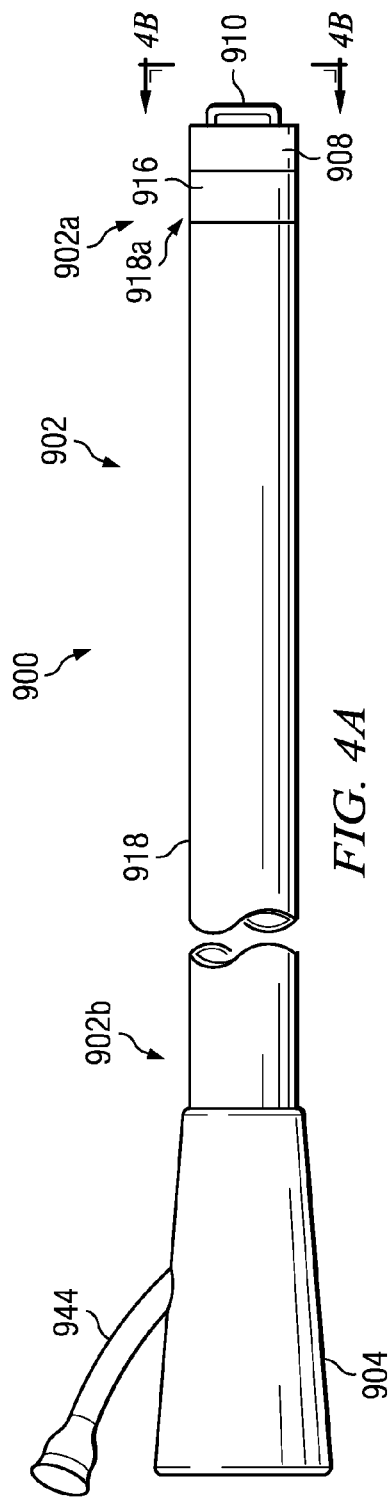
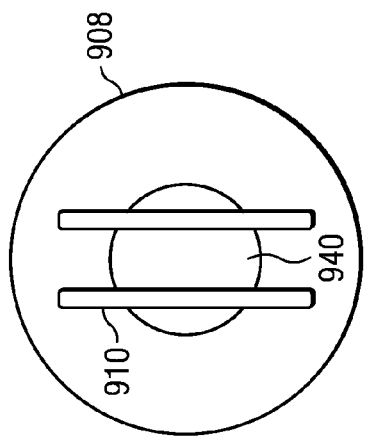
FIG. 4A
FIG. 4B

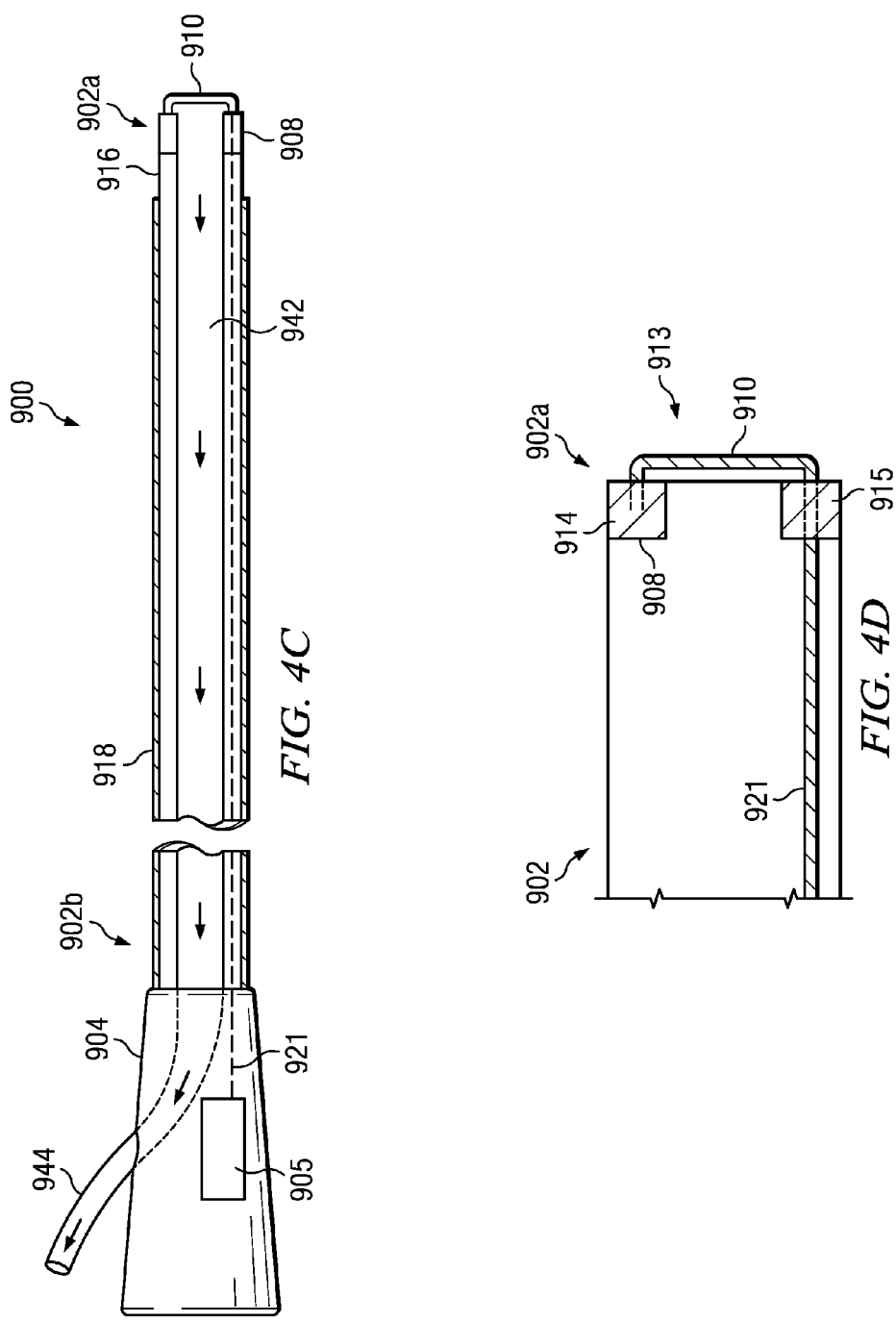

ELECTROSURGICAL SYSTEM AND METHOD FOR TREATING HARD BODY TISSUE

FIELD OF THE INVENTION

This invention pertains to electrosurgical systems and methods for treating tissue, in particular, an electrosurgical method for treating hard body tissues such as osseous or dental tissue, whereby an active electrode is directed to modify the hard body tissue and some surrounding tissue so as to augment the tissue preparation, and improve subsequent healing, remodeling and/or implant fixation.

BACKGROUND OF THE INVENTION

Careful and optimal preparation of a hard body tissue such as a portion of bone or tooth to receive an implant is key to a procedure's success. Many factors may affect the strength and overall outcome of the implant's performance, including the acute cleanliness and preparation of the tissue for acute implant fixation strength, as well as any preparation to promote bone healing and remodeling, necessary to promote desired fixation over time.

Wound healing is the body's natural response for repairing and regenerating tissue, which is generally categorized into four stages: 1) clotting/hemostasis stage; 2) inflammatory stage; 3) tissue cell proliferation stage; and 4) tissue cell remodeling or growth stage. In the case of bone, which has the ability to heal and remodel, the natural process starts when the injured bone and surrounding tissues bleed, forming what is often called fracture hematoma. The blood coagulates to form a blood clot situated between broken fragments of a fractured bone, or between an implant surface and bone, in the case of a bone implant procedure. This blood clot serves as a bridge or conduit for the healing and growth cells to travel, so as to preferably fuse pieces of bone, in the case of a fracture, or integrate the implant with the bone, in the case of a bone implant procedure. Within a few days blood vessels grow into the jelly-like matrix of the blood clot. The new blood vessels deliver phagocytes to the area, which gradually remove any non-viable material or debris such as dead or necrotic tissue or bacterial matter, which may otherwise obstruct or delay the wound from healing and bone from remodeling or growing. This clotting of blood activates platelets which in turn cause the release of a multiplicity of growth factors and cytokines, critical to wound healing, as they cause osteogenic cells (bone forming) to migrate to the wound site. The blood vessels also bring fibroblasts in the walls of the vessels and these multiply and produce collagen fibers. In this way the blood clot is replaced by a matrix of collagen.

At this stage, some of the fibroblasts begin to lay down bone matrix (calcium hydroxyapatite) in the form of insoluble crystals. This mineralization of the collagen matrix stiffens it and transforms it into bone that now connects the fractured bone together or the implant component to the bone in the case of an implant. This initial "woven" bone does not have the strong mechanical properties of mature bone. By a process of remodeling, the woven bone is replaced by mature "lamellar" bone. The whole process can take up to 18 months, but in adults the strength of the healing bone is usually 80% of normal by 3 months after the injury.

Bone remodels or grows as a natural reaction to being placed under repeated stress, such as weight bearing exercises. Stress on the bone result in the thickening of bone at the points of maximum stress. It is hypothesized that this is a result of the bone's piezoelectric properties, which cause bone to generate small electrical potentials under stress. This piezoelectrical property has also been used to promote bone growth, by the external application of an electrical field to areas of damaged bone during healing, described in more detail later.

Interruption or failure of the healing process may lead to the failure of the implant to connect (osseointegrate) with the resected bone or the failure of a bone fracture to fuse, and consequently an inferior procedural outcome and/or a possible additional surgery. A number of factors may overwhelm the body's ability to effectively heal a wound and for bone remodeling to occur, such as repeated trauma or tissue scarring, the use of nicotine, inadequate calcium uptake, osteoporosis, an overriding illness, or a restriction in blood supply to the bone resection or wounded area. Several factors can help or hinder the bone healing process. Bone shards can also embed in the adjacent muscle, often causing significant pain.

To promote osseointegration or fusion, surgeons today use a combination of techniques. One method includes introducing healthy bone cells such as those found in the patient's bone marrow into the area surrounding the implant component; however this requires the additional time and consequences of a secondary surgical site. Surgeons also commonly aid bone growth by providing scaffolding in which the bone can grow such as a calcium phosphate ceramic matrix or human bone. As an alternative, a surgeon may use a bone induction material; a material with the capacity of many normal chemicals in the body to stimulate primitive "stem cells" or immature bone cells (osteoblasts) to grow and mature, forming healthy bone tissue, faster than the body normally would. Most of these stimulants are protein molecules called, as a group, "peptide growth factors" or "cytokines". One group of proteins that has been used to cause osteoinduction is a genetically engineering protein called Bone Morphogenetic Proteins (BMP). However, this is a foreign substance that takes time to work with and may induce bone growth outside on the intended implant site. It has also been known to simulate tissue other than bone to grow.

Aside from BMPs, other growth factors including fibroblast growth factor (FGF), platelet-derived growth factor (PDGF) and transforming growth factor beta (TGF-β) may promote the division of osteoprogenitors, and potentially increase osteogenesis. UCB is another human recombinant protein that is currently under development, similar to BMP that helps control bone regeneration, but reportedly without some of the ectopic side-effect.

Referring now to FIG. 1A, an illustration of an exemplary hip joint 100 is shown including a femur bone 110 and pelvic bone 150. An exemplary artificial hip system 120 is partially installed and is shown in an exploded form for better explanation of the figure. Artificial hip system 120 may include an acetabular system 122 and femoral component 124. This illustration is shown with part of the femur and pelvic bone cut away to show resected and prepared areas 112 of the bone. As shown, femur 110 has been prepared to receive femoral component 124, commonly achieved by reaming or resecting the core of femur 110. Exemplary resected areas 112 are indicated. Femoral component 124 and resected femur 110 may be a pressfit together and the femoral component 124 surface may be roughened or treated to promote a stronger bone-to-implant integration. Alternatively, cement (not shown here) or implant coatings may be used to help provide a scaffold and provide for better osseointegration. Acetabular system 122 is formed to fit within a prepared acetablum 148 of the pelvic bone 150 and appropriately shaped resection tools, such as cupped reamers (not shown here) are available to the surgeon to prepare the acetabulum 148. Preparation of the acetabulum 148 may include scraping, cutting or drilling depending on the patient and exemplary resected areas 112 are shown. Acetabular system 122 may be fixed within acetabulum 148 using cement (not shown here) or through a pressfit. Bone screws 125 may be used to provide improved fixation. Acetabular system 122 and/or femoral component 124 may also have a porous coating or sintered surface (not shown here) to improve implant fixation with bone as the bone grows so as to integrate with the implant component. While screws and mechanical mean of fixation are used, bone remodeling so as to at least partially integrate with the implant component preferable to the long term success of the procedure.

Referring now to FIG. 1B, a knee joint 200 is shown, including a femur 205 and tibia 210 with a knee implant system 250 in place. During an implant procedure, femoral distal portion 206 may be resected and a knee femoral component 255 may be assembled as shown. Exemplary resected areas at the femoral distal portion are shown 260. Femoral component 255 may be attached to femoral distal portion 206 with cement or with a press fit, similar to that described in FIG. 1A. In addition tibial proximal portion 211 may also be resected to fit with a tibial knee component 270. Exemplary tibial resected areas 271 are shown. Some but not all tibial resected surfaces 271 are indicated on FIG. 1B. In between femoral component 255 and tibial component 270 a plate 275 may preferably be included. Plate 275 is adapted to allow femoral component 255 to rotate as the knee 200 articulates, with an appropriate feel and resistance, while plate 275 is preferably constructed from a very resilient and low friction material, such as high density polyethylene, reducing the effects of material wear over time. Similar to the hip implant system described earlier, while pressfits, screws, cements and other acute means of implant fixation are used by the surgeon, early and strong osseointegration is often an important factor in achieving a successful procedural outcome.

Referring now to FIG. 1C, an illustration is shown of a shoulder joint 300, including a humerus 310 and the socket portion or glenoid 320 which is part of the scapula 322. An exemplary replacement implant system 350 is shown in the illustration, often required due to pain from arthritis in the shoulder joint 300. The illustration is shown in an exploded form to better demonstrate the implant 350 and resected areas 314. During the procedure, the glenoid socket 320 is reamed or resected and holes 324 may be drilled so as to fit well with the matching shape of the glenoid socket implant 360. Bone screws (not shown here) may be used and inserted into drilled holes 324. The implant 360 may then be press fit into the prepared glenoid socket 320, and similar to previously discussed implants, the implant may have a variety of methods to improve the fixation of the implant. Porous or cancellous bone in the center of the humerus 310 is removed through reaming and general resection and the head of the humerus is removed. The stem implant 370 may then be inserted into the humerus canal and a variety of fixation means may be used, as discussed previously, to keep the stem implant in place and promote osseointegration. The ball implant 312 is then attached to the head of the humerus 310. This ball may be nested within the glenoid implant 360.

Referring now to FIG. 1D, an exploded illustration of a root form dental implant 400 is shown including the jaw bone 410, dental implant system 415 and two natural teeth 425 with teeth roots 420. Dental implant system 415 includes an implant root 430, an implant post 435 and a crown 438. The implant root 430 screws into the jaw bone 410, to fit within the jaw bone 410 similar to a natural tooth root 420. The implant root is typically constructed from titanium and before insertion into the bone 410 a tunnel 450 is typically drilled or resected to prepare the bone 410 to receive the implant root 430.

As with all the implant systems described earlier, in order for this implant system 415 to succeed, the surface of the drilled tunnel 450 and any other surrounding and supporting bone 410 should preferably partially heal, remain healthy, and a portion should osseointegrate with the implant root 430. The patient's body will naturally aid this healing and growth process through the pressure from chewing on the implant crown 438 transmitting to the underlying bone 410. However, the dental patient may not always have healthy underlying jaw bone 410 due to previous extractions, injuries, cysts or infections. Jaw bone grafting or jaw bone augmentation may be needed to supplement the implant procedure and improve procedural outcome. There are also other dental implant system designs that require less jaw bone 410, not described here, including blade implants that have a narrower root region for areas of reduced jaw bone. Alternatively a method of augmenting the existing jaw bone may be used.

FIG. 1E shows an illustration of an exemplary fractured bone 505 with a plate system attached 500, shown in exploded form to better demonstrate the resected areas. An exemplary bone fracture 510 is shown with a plate 550 and bone screws 555 assembled to secure plate 550. This plate 550 is intended to help maintain the bone 500 and fracture 510 in the correct position and support the bone as the fracture 510 heals. There are many forms of bone fracture in many areas of the body with a variety of bone plates, support structures and screws that may be used in a similar fashion with a similar intent, to the one described above.

Plate 550 may be attached to bone 500 through drilled bone tunnels 560 prepared to receive at least one bone screw 555. Bone screws 555 may be used in conjunction with cement to improve the interface strength between the bone 500 and screw 555. Assuming plate 550 and bone screws 555 are intended to be permanent fixtures in the patient, the long-term success of this medical procedure will significantly impacted by the ability of the fractured bone 510 to heal and the plate 550 and screws 555 to maintain a strong bond or osseointegrate with the surrounding bone areas, such as drilled surfaces 561 and prepared outer bone surface 551. Outer bone surface 551 may be prepared to receive the plate 550 so as to form a better mating surface with the plate and help augment the implant-to-bone fusion process. Fracture 510 may also be cleaned of debris, if the fracture is accessible.

FIG. 1F illustrates an example of an autogenous bone grafting harvest, where an autogenous bone graft 605 may be taken from a harvest site 600, leaving exposed bone surfaces 630. Here an exemplary site is a patient's iliac crest 610, although other areas are also used such as the mandibular symphysis (chin area), fibula or ribs. The bone graft 605 may then be utilized in a patient' spine or jaw, a bone fracture site or any other area to provide bone producing cells and scaffolding to assist in the healing and bone growth. Thereafter, two areas exist where bone needs to heal and grow. In this example, the graft 605 itself as well as the harvest site resected area 630. The area of harvest is often problematic post surgery, associated with high donor morbidity and it can be the source of significant pain, often more than the pain from the primary surgical site. Over time, the exposed area 630 is expected to heal, remodel and fuse back together, which does not always happen reliably.

Additionally, there are many other bone implants and portions of bone not described here in detail where bone repair and remodeling is preferable. These include, but are not limited to soft tissue anchors, ligament graft anchors or screws within a bone tunnel, elbow and hand implants, spinal implants and bone fractures throughout the body.

FIG. 1G shows an exploded illustration of a dental crown or cap 650. Crown 650 is often used to repair a fractured or weakened tooth that can no longer receive a dental filling. Typically the original tooth 660 is shaped and made smooth and any plaque or decayed tooth in removed, so as to receive the crown 650, using a variety of dental tools such as a dremel or drill. Exemplary prepared surfaces 655 are shown. Cap 650 may have been prepared earlier to match the patient's bite and size requirements and may be slipped over the tooth 660 and cement or a fixative (not shown here) may be used to keep the crown in place. Cap 650 is usually made from a metal alloy, porcelain or dental ceramic. Since teeth do not grow or remodel, this fixative is expected to retain the crown 650 in position for the lifetime of the cap 650. Therefore a great deal of attention is paid to the tooth surface 655 to ensure it is clean and sterile to maximize the connection strength and reduce any likelihood of infection, in the area between the crown 650 and tooth 660 over time.

Accordingly, there remains a need for new and improved methods for use in preparation for hard body tissues to receive an implant. In the case of bone tissue a need for a new and improved method to preferably promote the repair and subsequent bone growth is needed to address certain of difficulties aforementioned. It is therefore an objective to provide methods and systems to facilitate these goals.

SUMMARY OF THE INVENTION

According to one embodiment, a method for preparing a target bone to receive an implant component including positioning an active electrode in proximity to a target bone tissue and proximate an electrically conductive fluid followed by applying a high frequency voltage between the active electrode and a return electrode, where the high frequency voltage is sufficient to form a plasma, is disclosed. The plasma modifies at least a portion of the target bone tissue. An implant component is then disposed adjacent at least a portion of the modified target bone tissue. In certain embodiments the target bone tissue is a resected portion of bone. Modification of the bone tissue may include inducing blood flow to the tissue, removing biofilm or bacteria from the target tissue, debriding the tissue, creating a tissue surface geometry beneficial for enhanced bonding of implants, sterilizing the tissue, invoking a gene expression in the target tissue, eliciting a change in the metabolic response of the tissue, eliciting a biochemical response in the tissue, and eliciting a physiological response in the tissue.

In another embodiment, a method of electrosurgical treatment of bone tissue including positioning an active electrode in proximity to a target bone tissue and an electrically conductive fluid is disclosed. The method includes applying a high frequency voltage between the active electrode and a return electrode, the high frequency voltage being sufficient to form a plasma, wherein the plasma modifies the target bone tissue and stimulates bone repair. In certain embodiments the target bone tissue is bone exposed following a resection of a portion of bone so as to receive and grow into an implant component.

In another embodiment, a method of preparing a target bone tissue is disclosed, including positioning an active electrode in proximity to a target bone tissue and proximate an electrically conductive fluid, wherein the target tissue is being prepared to receive an implant component. A high frequency voltage is applied between the active electrode and a return electrode, the high frequency voltage sufficient to form a plasma and modify at least a portion of the bone tissue. Modification of the bone tissue may include, but is not limited to inducing blood flow to the tissue, removing biofilm or bacteria from the target tissue, debriding the tissue, sterilizing the tissue, invoking a gene expression in the target tissue, eliciting a change in the metabolic response of the tissue, eliciting a biochemical response in the tissue, and eliciting a physiological response in the tissue.

In another embodiment, a method of treating bone tissue is disclosed that includes positioning an active electrode in proximity to a target bone tissue and applying a high frequency voltage between the active electrode and a return electrode. This high frequency voltage is preferably sufficient to develop a high electric field intensity associated with a vapor layer proximate the active electrode, wherein the high field intensity stimulates the secretion of at least one growth mediator associated with bone repair.

In another embodiment, a method is disclosed that includes the preparation of a target bone tissue. The method includes positioning an active electrode in proximity to a target bone tissue and proximate an electrically conductive fluid, wherein the target tissue is being prepared to receive an implant component; applying a high frequency voltage between the active electrode and a return electrode, the high frequency voltage is sufficient to form a plasma, wherein the plasma applies an electrical field to at least a portion of the target bone tissue to stimulate bone repair and growth.

In another embodiment, a method is disclosed that includes preparing a target dental tissue to receive an implant including positioning an active electrode in proximity to the target dental tissue and proximate an electrically conductive fluid followed by applying a high frequency voltage between the active electrode and a return electrode, where the high frequency voltage is sufficient to form a plasma and thereby modify at least a portion of the target tissue. An implant is then disposed adjacent at least a portion of the modified target dental tissue.

In certain embodiments, an electrically conductive fluid is provided proximate the active electrode, such that the fluid is vaporized and ionized to thereby form a plasma. Modification of the target hard body tissue in accordance with the present method may include perforating tissue on and in the vicinity of the target tissue. Modification may also support the debridement and/or sterilization of the bone tissue. For example, in the case of resected bone tissue, modification may include the debridement of necrotic or damaged tissue from the resection process, both on the periphery and within the resection area itself, so as to prepare and sterilize it, to optimize wound healing and ingrowth to the implant. In addition, modifying target tissue may include removing biofilm and bacteria from a fracture or resected area or treating biofilm or bacteria to render it inert. In some embodiments modifying the target tissue may include sterilizing portions of a tooth and preparing the area so as to better prepare it to receive a dental cap or filling. Applying plasma and associated RF electric energy may preferably induce, stimulate or otherwise encourage a metabolic, biochemical, and/or physiological change in the bone or dental tissue and surrounding tissue, and thereby leverage the body's natural healing response to encourage ingrowth into an implant.

Various electrode configurations may be utilized according to the desired manner of treatment of the tissue. In certain electrode configurations, an electrically conductive fluid may is preferably provided proximate the active electrode to generate plasma. Depending on the apparatus used, the conductive fluid may be provided by a fluid delivery lumen that discharges the fluid in the vicinity of the target tissue. The fluid delivery lumen may be integrated with the electrosurgical instrument or may be provided separately. Alternatively, a conductive gel or other medium may be applied to the target tissue prior to treatment. Similarly, in some embodiments, an aspiration lumen may be provided to remove electrically conductive fluid, body tissue and resulting gases from the vicinity of the target tissue.

In using high electric field intensities associated with a vapor layer to modify the bone tissue, the present method utilizes the RF electric energy to stimulate healing and bone repair, remove necrotic or unhealthy tissue as well as biofilm and bacteria, and improve blood flow to the treated tissue and promote bone-ingrowth with an implant. The use of plasma to stimulate healing and modify wound tissue through removal of necrotic tissue also leverages the body's cytokine role in coordinating inflammatory response and repairing tissue as described in "Percutaneous Plasma Discectomy Stimulates Repair In Injured Intervertebral Discs," Conor W. O'Neill, et al, Department of Orthopedic Surgery, Department of Radiology, University of California, San Francisco, Calif. (2004), incorporated herein by reference.

As noted in the O'Neil reference, electrosurgical plasma alters the expression of inflammatory response in tissue, leading to a decrease in interlukin-1 (IL-1) and an increase in interlukin-8 (IL-8). While both IL-1 and IL-8 have hyperalgesic properties, IL-1 is likely to be the more important pathophysiologic factor in pain disorders than IL-8. Also, as described in the O'Neil reference, cytokines play an important role in coordinating inflammatory and repair response to tissue injury. For example, IL-1 is a catabolic mediator that induces proteases and inhibits extra-cellular matrix synthesis. On the other hand, IL-8 is anabolic as it promotes a number of tissue repair functions including formation of provisional extra-cellular matrices, angiogenesis, fibroblast proliferation and differentiation, stem cell mobilization, and maturation and remodeling of extra-cellular matrices.

The effect of an electrosurgical system and its method for treating chronic wound tissue has been described in U.S. patent application Ser. No. 12/430,181, filed Apr. 27, 2009, and entitled "Electrosurgical System and Method for Treating Chronic Wound Tissue," which is a continuation-in-part of prior U.S. patent application Ser. No. 11/327,089, filed Jan. 6, 2006, and entitled "Electrosurgical Method and System for Treating Foot Ulcer," both applications hereby incorporated herein by reference.

These above references describe the alteration of the expression of cytokines such that there is a decrease in IL-1 and an increase in IL-8, it is disclosed that plasma may preferably stimulate a healing response mediated by IL-8 to mediate tissue regeneration, resulting in overall tissue healing, and a decrease in inflammation and pain. Increased IL-8 levels attributable to the presently described electrosurgical procedures may also play a role in enhanced sterilization of the target tissue as a result of the higher rate of neutrophil attraction to the treated tissue. Neutrophils produce reactive oxygen species (ROS) that combat infection and kill bacteria colonizing a wound bed, such that increased attraction of neutrophils through the resultant higher IL-8 levels described above may have a sterilizing role through addressing wound infection and bacteria levels, as well as limiting the possibility of extended inflammation in the wound tissue that delays healing and further damages tissue associated with chronic wounds. Furthermore, the presence of increased levels of IL-8 may assist in counteracting the fibroblast gene expression characteristic in chronic wounds that is attributed to failure of the fibroblast to produce an adequate metabolic response to epithelialize the wound or resected area.

Similarly, enhancement of several key biochemical markers is a significant aspect of proper bone repair and subsequent osseointegration. Growth factors are imperative in successful wound healing, and inadequate growth factor levels can be a significant contributor in osseointegration. By utilizing the effects of electrosurgical ablation according to the presently described methods to stimulate one or more growth factors such as vascular endothelial growth factor (VEGF), insulin-like growth factor (IGF), and epidermal growth factor (EGF), the proliferation, migration to the resected bone area, and production of new extracellular matrix components by fibroblasts may be preferably encouraged. Furthermore, treatment of fractured or resected bone tissue with the electrosurgical ablative procedures described herein may also beneficially increase sterility as well as promote formation of collagen and granulation tissue as part of the reepithelialization phase of bone repair.

The temperature effect of electrosurgical ablation according to the presently described methods may also have an influence on an improved wound healing response and subsequent bone remodeling. During the ablative process, a steep temperature gradient away from the electrosurgical probe may preferably be created, suggesting that a majority of the tissue cells in the vicinity of the electrically conductive fluid are preferably exposed to non-fatal cell stress. However, in correlation to the limited temperature effect is an observation of elevated levels of heat shock proteins such as heat shock protein-70 (Hsp70). As described in "The Short Term Effects of Electrosurgical Ablation on Proinflammatory Mediator Production by Intervertebral Disc Cells in Tissue Culture," Kee-Won Rhyu, et al, Department of Orthopedic Surgery, Department of Radiology, University of California, San Francisco, Calif. (2007), incorporated herein by reference, the level of Hsp70 of treated cells was transiently increased after ablation and may have been induced by the non-fatal cell stress effected by ablation. Changes in Hsp70 levels indicate that ablation may alter the cell stress environment, and that ablation may be tied to elevating Hsp70 activity responsible for cellular recovery, survival, and maintenance of normal cellular function.

The methods described herein for promoting a bone repair response may result in a variety of biochemical, metabolic, physiological, or anatomical changes that invoke a stabilized healing response to the treated tissue. The desired response may be attributed to numerous factors, including gene expression, nerve stimulation, stimulation of greater blood flow, collagen growth, alteration of cellular function, treatment site sterilization, or other biochemical or metabolic events that promote healing, repair, and regeneration of injured tissue. In some embodiments, these induced changes may include increased anabolic tissue cellular response including angiogenesis, fibroblast proliferation, and stabilized remodeling of extra-cellular matrices. The changes may further include increased nerve stimulation, cell metabolism, increased collagen synthesis in fibroblasts, transformation of fibroblasts to myofibroblasts, increased capillary formation with enhanced microcirculation, and/or enhanced clearance of noxious substances associated with the inflammatory response. In other embodiments, the bone repair response may include an increased blood flow to, and vascularization or revascularization of, the treated fractured or resected region, thereby promoting healing and regeneration of bone tissue.

Bone tissue is unique in that it has been shown to have a steady state electrical potential, that is significantly electronegative at the site of growing bone, as described in "McGlamry's Comprehensive Textbook of Foot and Ankle Surgery, Volume 2", Banks, A. S et al., incorporated herein by reference. It has been found therefore that applying electronegative currents may induce osteogeneration. Electrical fields and electromagnetic fields are also described in "Bone regeneration and repair: Biology and clinical applications", Liebermann, Jay R. et al., incorporated herein by reference as stimulation techniques for fracture healing and bone repair. Additionally, electro-magnetic fields have been shown to affect both sign transduction pathways and growth factor synthesis and they appear to result in the up-regulation of growth factor production or the stimulation of growth factor secretion. Electrical fields are described as having shown some effect on calcium-ion transport cell proliferation, IGF-2 release and IGF-2 receptor expression on osteoblasts, the cell required for osteogeneration.

Embodiments of the present methods and system are described and illustrated in the following detailed specification.

BRIEF DESCRIPTION OF THE DRAWINGS

FIGS. 4A, 4B, 4C and 4D and 4E are illustrations of an alternative embodiment of an electrode configuration for preparing a portion of hard body tissue in accordance with at least some of the embodiments of the present method;

NOTATION AND NOMENCLATURE

Figure 1A:
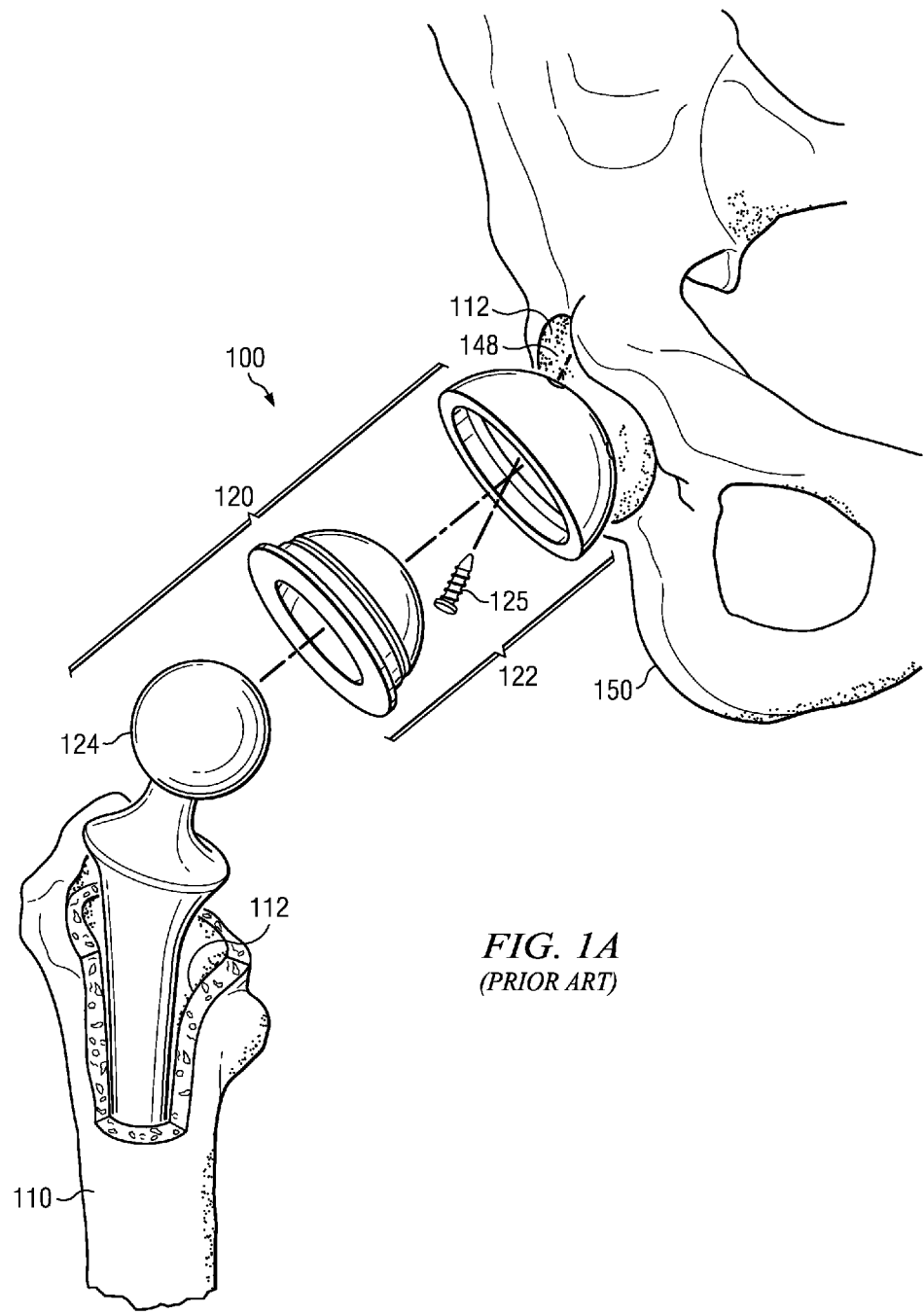
FIG. 1A is a prior art illustration, shown in an exploded form, of a hip with hip implant components in-situ.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical device which produces an electrically-induced tissue-altering effect when brought into contact with, or close proximity to, a tissue targeted for treatment, and/or an electrode having a voltage induced thereon by an electrosurgical generator.

"Return electrode" shall mean an electrode of an electrosurgical wand which serves to provide a current flow path for electrons with respect to an active electrode, and/or an electrode of an electrosurgical wand which preferably does not itself produce an electrically-induced tissue-altering effect on tissue targeted for treatment.

"Growth mediator" shall mean mechanisms associated with bone repair and growth that may be expressed by the body during repair and bone growth, including but not limited to cytokines, interleukin (IL)-8, vascular endothelial growth factor (VEGF), insulin-like growth factor (IGF), epidermal growth factor (EGF), and heat shock protein-70 (Hsp70), fibroblast growth factor (FGF), platelet-derived growth factor (PDGF) and transforming growth factor beta (TGF-β) which may promote the division of osteoprogenitors, and potentially increase osteogenesis.

"Resection" shall mean the preparation or shaping of hard tissue such as dental or osseous tissue "bone", including but not limited to drilling, reaming, scrapping, rasping, clipping or cutting.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION OF THE INVENTION

In the drawings and description that follows, like parts are marked throughout the specification and drawings with the same reference numerals, respectively. The figures herein are not necessarily to scale. Certain features of the invention may be shown exaggerated in scale or in somewhat schematic form and some details of conventional elements may not be shown in the interest of clarity and conciseness. The present invention is susceptible to embodiments of different forms. Specific embodiments are described in detail and are shown in the drawings, with the understanding that the present disclosure is to be considered an exemplification of the principles of the invention, and is not intended to limit the invention to that illustrated and described herein. It is to be fully recognized that the different teachings of the embodiments discussed below may be employed separately or in any suitable combination to produce desired results.

Electrosurgical apparatus and systems adaptable for use with the present method are illustrated and described in commonly owned U.S. Pat. Nos. 6,296,638; 6,589,237; 6,602,248 and 6,805,130, U.S. patent application Ser. No. 11/770,555 by Davison and U.S. Pat. No. 7,241,293, the disclosures of which are herein incorporated by reference. Examples of electrosurgical devices which may be used with the present method include SpineVac®, Aggressor®, Discoblator, TL SpineWand® (in development), Super TurboVac®, UltraVac®, Evac® 70 and Topaz® electrosurgical devices manufactured by ArthroCare Corporation. In one exemplary embodiment illustrated in FIG. 2, the electrosurgical system 708 may include a probe 710 comprising an elongated shaft 712 and a connector 714 at its proximal end, and one or more active electrodes 716a disposed on the distal end of the shaft. Also disposed on the shaft but spaced from the active electrode, there may be a return electrode 716b. Alternatively this may be placed on the patient body. A handle 720 with connecting power cable 718 and cable connector 722 may be removably connected to the power supply 726.

As used herein, an active electrode is an electrode that is adapted to generate a higher charge density relative to a return electrode, and hence operable to generate a highly ionized vapor layer which may also be referred to as a plasma in the vicinity of the active electrode when a high-frequency voltage potential is applied across the electrodes, as described herein. Typically, a higher charge density is obtained by making the active electrode surface area smaller relative to the surface area of the return electrode.

Power supply 726 may comprise selection controls 728 to change the applied voltage level. The power supply 726 may also include a foot pedal 732 positioned close to the user for energizing the electrodes 716a, 716b. The foot pedal 732 may also include a second pedal (not shown) for remotely adjusting the voltage level applied to electrodes 716a, 716b. Alternative embodiments may have a handswitch on the probe 710. Also shown in the figure is an optional electrically conductive fluid supply 736 with tubing 734 for supplying the probe 710 and the electrodes with electrically conductive fluid. Details of a power supply that may be used with the electrosurgical probe of the present invention is described in commonly owned U.S. Pat. No. 5,697,909, which is hereby incorporated by reference herein.

Figure 2:
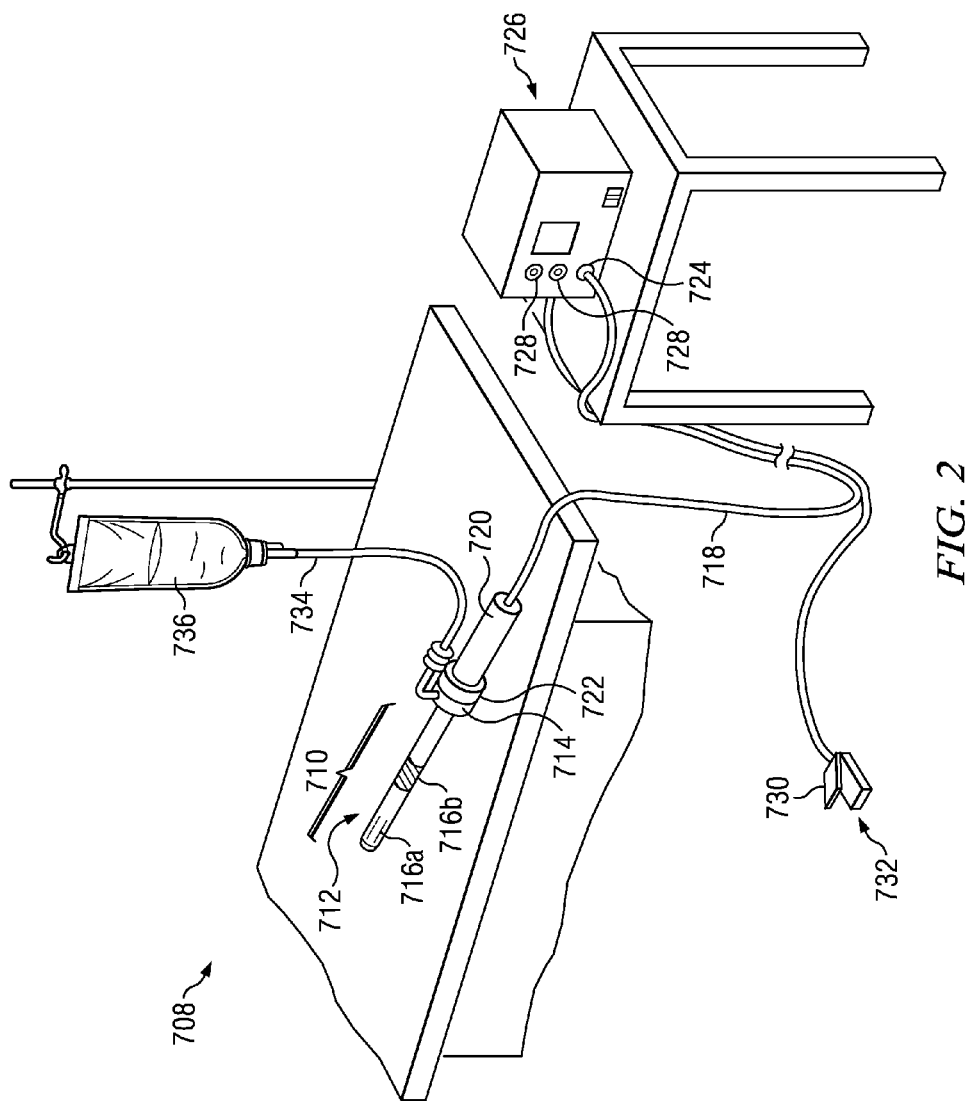
FIG. 2 is an illustration of an electrosurgical system adaptable for use with at least some of the embodiments of the present method.

As illustrated in FIG. 2, the return electrode 716b is connected to power supply 726 via cable connectors 718. Typically, return electrode 716b is spaced at about 0.5 mm to 10 mm, and more preferably about 1 mm to 10 mm from active electrode 716a. Shaft 712 is disposed within an electrically insulative jacket, which is typically formed as one or more electrically insulative sheaths or coatings, such as polyester, polytetrafluoroethylene, polyimide, and the like. The provision of the electrically insulative jacket over shaft 712 prevents direct electrical contact between shaft 712 and any adjacent body structure or the user. Such direct electrical contact between a body structure and an exposed return electrode 716b could result in unwanted heating of the structure at the point of contact, possibly causing necrosis or other unintended tissue effects.

As will be appreciated, the above-described systems and apparatus may be applied equally well to a wide range of electrosurgical procedures including open procedures, intravascular procedures, urological, laparoscopic, arthroscopic, thoracoscopic or other cardiac procedures, as well as dermatological, orthopedic, gynecological, otorhinolaryngological, spinal, and neurologic procedures, oncology and the like. However, for the present purposes the system and methods described herein are directed to prepare a target hard body tissue such as osseous or dental tissue, including but not limited to dental tissue or any cancellous bone or cortical bone including a femur, an acetabulum, a knee, a scapula, a tibia, a humerus, a vertebral body, a fracture site implant, a bone plate site and a bone graft site as well as any surrounding tissues such as any hematoma or damaged tissue.

The assignee of the present invention developed Coblation® technology. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid and form a vapor layer over at least a portion of the active electrode(s) in the region between the tip of the active electrode(s) and the target tissue. The electrically conductive fluid may be a liquid or gas, such as isotonic saline, Ringers' lactate solution, blood, extracellular or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by directing radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer. Once the ionic particles in the plasma layer have sufficient energy, they accelerate towards the target tissue. This ionization, under these conditions, induces the discharge of plasma comprised of energetic electrons and photons from the vapor layer and to the surface of the target tissue. Energy evolved by the energetic electrons (e.g., 3.5 eV to 5 eV) can subsequently bombard a molecule and break its bonds, dissociating a molecule into free radicals, which then combine into final gaseous or liquid species. Among the byproducts of this type of ablation are hydroxyl radicals, which have been shown to influence IL-8 expression. See Rhyu, "Short Term Effects of Electrosurgical Ablation," at 455. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), tissue structures are preferably volumetrically removed through molecular disintegration of larger organic molecules into smaller molecules and/or atoms, such as hydrogen, oxygen, oxides of carbon, hydrocarbons and nitrogen compounds; the effect of molecular dissociation may be significantly more pronounced with respect to soft tissue structures than with respect to dental tissue or bony tissue. The treatment of such harder tissue with the plasma described here in may result in any of a) a removal of all adjacent soft tissue b) the volumetric removal of a portion of the harder tissue, or c) minimal or no observable removal of the harder tissue, but nonetheless a stimulation of the harder tissue sufficient to prepare the harder bone for receiving an implant. A more detailed description of these phenomena, termed Coblation®, can be found in commonly assigned U.S. Pat. Nos. 5,683,366 and 5,697,882, the complete disclosures of which are incorporated herein by reference.

In certain embodiments of the present method, the applied high frequency voltage can be used to modify tissue in several ways, e.g., current may be passed directly into the target site by direct contact with the electrodes to heat the target site; or current can be passed indirectly into the target site through an electrically conductive fluid located between the electrode and the target site also to heat the target site; or current can be passed into an electrically conductive fluid disposed between the electrodes to generate plasma for treating the target site. In accordance with the present method, the system of FIG. 2 is adaptable to apply a high frequency (RF) voltage/current to the active electrode(s) in the presence of electrically conductive fluid to modify or otherwise treat the tissue on and in the vicinity of resected or fractured bone or dental tissue. Thus, with the present method, the system of FIG. 2 can be used to modify tissue by: (1) inducing blood flow to the target bone tissue; (2) cleaning local debris from the damaged or resected tissue; (3) invoking a gene expression in the target bone tissue; (3) eliciting a change in the metabolic response of the target bone tissue; (4) eliciting a biochemical response in the target bone tissue; (5) eliciting a physiological response in the target bone tissue; (6) sterilizing the damaged or resected tissue by removing or treating biofilm and bacteria from the area and/or (6) stimulating osteogenesis in the bone tissue.

In various embodiments of the present method, the electrically conductive fluid possesses an electrical conductivity value above a minimum threshold level, in order to provide a suitable conductive path between the return electrode and the active electrode(s). The electrical conductivity of the fluid (in units of milliSiemens per centimeter or mS/cm) is usually be greater than about 0.2 mS/cm, typically greater than about 2 mS/cm and more typically greater than about 10 mS/cm. In an exemplary embodiment, the electrically conductive fluid is isotonic saline, which has a conductivity of about 17 mS/cm.

Also in various embodiments of the preset method, it may be necessary to remove, e.g., aspirate, electrically conductive fluid and/or ablation by-products from the surgical site. In addition, it may be desirable to aspirate small pieces of tissue that are not completely disintegrated by the high frequency energy, or other fluids at the target site, such as blood, mucus, small bone fragments and other body fluids. Accordingly, in various embodiments the present system includes one or more aspiration lumen(s) in the shaft, or on another instrument, coupled to a suitable vacuum source for aspirating fluids from the target site. In various embodiments, the instrument also includes one or more aspiration active electrode(s) coupled to the aspiration lumen for inhibiting clogging during aspiration of tissue fragments from the surgical site. A more complete description of these embodiments can be found in commonly owned U.S. Pat. No. 6,190,381, the complete disclosure of which is incorporated herein by reference for all purposes.

In certain embodiments of the present method, a single electrode or an electrode array may be disposed over a distal end of the shaft of the electrosurgical instrument to generate the plasma that is applied to the target tissue. In most configurations, the circumscribed area of the electrode or electrode array will generally depend on the desired amount and location of tissue to be treated. Exemplary instruments include ArthroCare's SpineVac® and Aggressor® surgical devices described in a co-pending U.S. patent application Ser. No. 11/770,555 and ArthroCare's UltraVac® surgical device, described in U.S. Pat. No. 7,241,293, both herein incorporated by reference. Other exemplary instruments include the Discoblator™, and Super TurboVac® surgical devices. In one embodiment, the area of the electrode or electrode array is in the range of from about 0.10 mm2 to 40 mm2, preferably from about 0.5 mm2 to 10 mm2, and more preferably from about 0.5 mm2 to 5.0 mm2.

In addition, the shape of the electrode at the distal end of the instrument shaft will also depend on the size of the tissue surface area to be treated. For example, the electrode may take the form of a pointed tip, a solid round wire, or a wire having other solid cross-sectional shapes such as squares, rectangles, hexagons, triangles, star-shaped, or the like, to provide a plurality of edges around the distal perimeter of the electrodes. Alternatively, the electrode may be in the form of a hollow metal tube or loop having a cross-sectional shape that is curved, round, square, hexagonal, rectangular or the like. The envelope or effective diameter of the individual electrode(s) ranges from about 0.05 mm to 6.5 mm, preferably from about 0.1 mm to 2 mm. Furthermore, the electrode may be in the form of a screen disposed at the distal end of the shaft and having an opening therethrough for aspiration of excess fluid and ablation byproducts or debris.

Figure 3A:
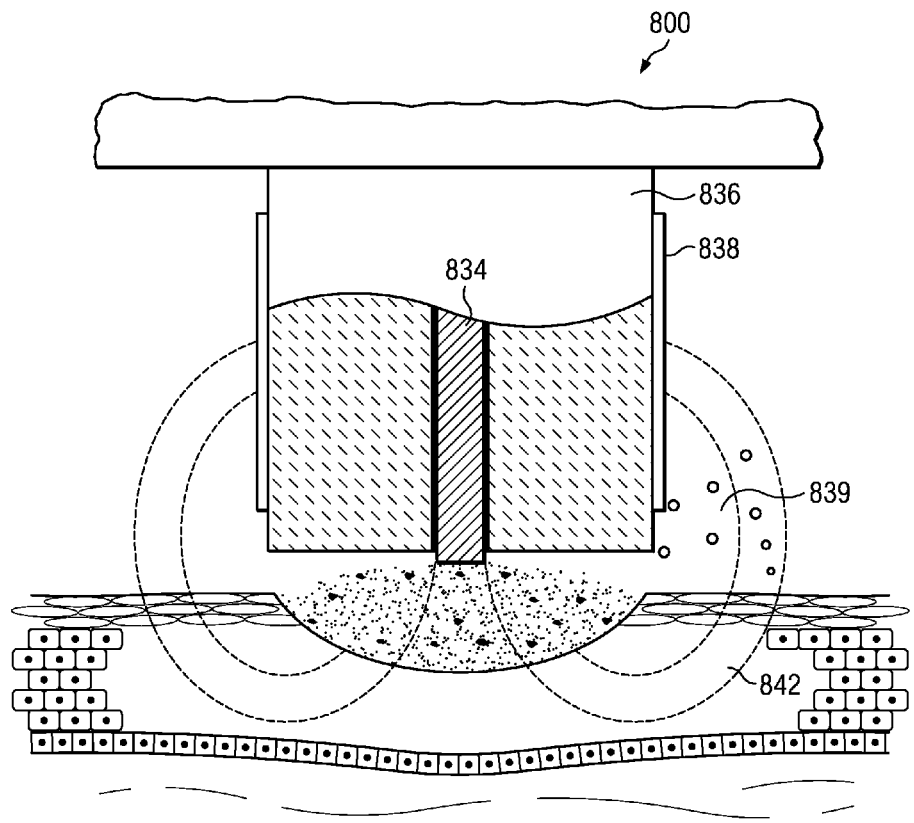
FIGS. 3A and 3B is an illustration of an exemplary electrode configuration for preparing a portion of hard body tissue in accordance with at least some of the embodiments of the present method.

Examples of an electrosurgical apparatus that can be used to modify tissue in accordance with the present method are illustrated in FIGS. 3A, 3B, and 4A-E. With reference to FIG. 3A, in one embodiment the apparatus 800 utilized in the present method comprises an active electrode 834 disposed on the distal end of a shaft 836. Spaced from the active electrode 834 is a return electrode 838 also disposed on the shaft 836. Both the active 834 and return electrodes 838 are connected to a high frequency voltage supply (not shown). An electrically conductive fluid is disposed proximate the active electrode 834 and return electrode 838. In one embodiment the electrically conductive fluid 839 forms an electrically conductive fluid path between the electrodes (834 and 838), thereby providing a preferred path for the flow of electrical current between active electrode 834 and return electrode 838. On application of a high frequency voltage across the electrodes, plasma is generated as described above, for use in treating hard tissue including bone tissue and dental tissue, in accordance with the present method as well as the selective ablation of soft tissue proximate the hard tissue that is necessary to prepare the hard tissue. A more detailed description of the electrical operation of the electrode configuration illustrated in FIG. 3A can be found in commonly assigned U.S. Pat. No. 6,296,638, the complete disclosure of which is incorporated herein by reference. Advantageously, as the tip of the electrode 834 presents a relatively broad surface area, the electrode tip illustrated in FIG. 3A may be beneficially used for treating larger tissue areas.

Figure 3B:
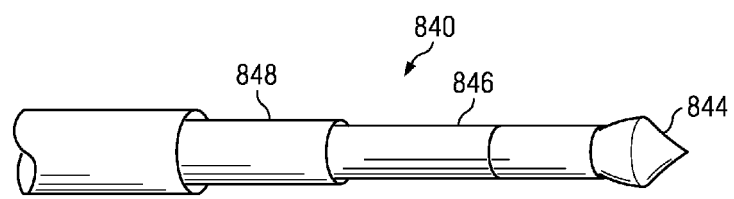

Similarly, with reference to FIG. 3B, in one embodiment the apparatus 840 utilized in the present method comprises an active electrode 844 disposed on the distal end of a shaft 846. Spaced from the active electrode 844 is a return electrode 848 disposed proximally from the active electrode 844. Both active electrode 844 and return electrode 848 are connected to a high frequency voltage supply (not shown). On application of a high frequency voltage across the electrode in the presence of a conductive fluid, plasma is generated proximate active electrode 844 for use in treating hard body tissue in accordance with the present method. A more detailed description of the electrical operation of the electrode illustrated in FIG. 3B can be found in commonly assigned U.S. Pat. No. 6,602,248, the complete disclosure of which is incorporated herein by reference. Advantageously, as the tip of the electrode 834 presents a narrow surface, the electrode tip of FIG. 3B may beneficially be used to more precisely treat smaller areas of tissue. In some embodiments, electrode 834 may create perforations, induce blood flow or create a small area of targeted electrical field-based tissue stimulation.

With reference to FIG. 4A, in one embodiment an electrosurgical instrument such as apparatus 900 is utilized in the present method and comprises shaft 902 having a shaft distal end portion 902a and a shaft proximal end portion 902b, the latter affixed to handle 904. An aspiration lumen 944, adapted for coupling apparatus 900 to a vacuum source (not expressly shown), is joined at handle 904 and is in fluid communication with aspiration lumen 940 shown in FIG. 4B. An electrically insulating electrode support 908 is disposed on shaft distal end portion 902a, and two active electrodes 910 are arranged on electrode support 908. In alternative embodiments a single active electrode or multiple active electrodes may be provided. An insulating sleeve 918 may cover a portion of shaft 902. An exposed portion of shaft 902 located between sleeve distal end 918a and electrode support 908 defines a return electrode 916. In the present preferred embodiments, return electrode 916 has a larger surface area then the collective surface area of active electrodes 910. In alternate embodiments, return electrode may comprise a separate component from shaft 902, and shaft 902 may be constructed from a non-conductive material.

Referring now to FIG. 4B, active electrodes 910 are arranged substantially parallel to each other on electrode support 908. Active electrodes 910 usually extend away from electrode support 908 to facilitate debridement, modification and ablation of tissue. A void within electrode support 108 defines aspiration port 940. Typically, active electrodes 910 span or traverse aspiration port 940, wherein aspiration port 940 is substantially centrally located within electrode support 908. Aspiration port 940 is in fluid communication with aspiration lumen 942 (FIG. 4C) for aspirating unwanted materials or debris from a treatment site.

Referring now to FIG. 4C, a cross-sectional view of apparatus 900) is shown. Aspiration lumen 942 is in fluid communication at its proximal end with aspiration tube 944. Aspiration port 940, aspiration channel 942, and aspiration tube 944 provide a suction unit or element for drawing pieces of tissue toward active electrodes 910 for further modification after they have been removed from the target site, and for removing unwanted materials such as ablation by-products, blood, or excess saline from the treatment field. Handle 904 houses a connector 905 adapted for independently coupling active electrodes 910 and return electrode 916 to a high frequency power supply. An active electrode lead 921 couples each active electrode 910 to connection block 905. Return electrode 916 is independently coupled to connection block 905 via a return electrode connector (not shown). Connection block 905 thus provides a convenient mechanism for independently coupling active electrodes 910 and return electrode 916 to a power supply (e.g., power supply 726 in FIG. 2). Connector 905 may connect directly to a high frequency power supply via an integrated cable or may connect via a separate cable component (not expressly shown).

Referring now to FIG. 4D, a cross-sectional view of shaft distal end 902a is shown. In certain embodiments, active electrode 910 includes a loop portion 913, a free end 914, and a connected end 915. Active electrode 910 is in communication at connected end 915 with active electrode lead 921 for coupling active electrode 910 to connection block 905. Alternatively, the active electrodes may be arranged in a screen electrode configuration, as illustrated and described in commonly owned U.S. Pat. Nos. 6,254,600 and 7,241,293, the disclosures of which are herein incorporated by reference.

Figure 4E:
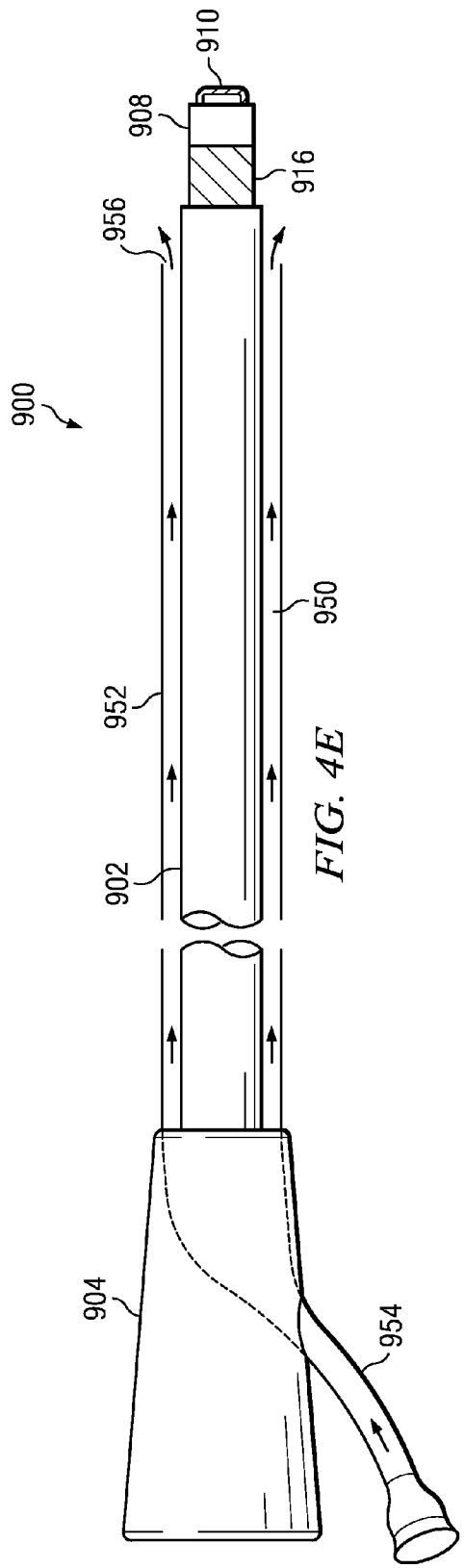

Referring now to FIG. 4E, in electrosurgical apparatus 900 is characterized by outer sheath 952 external to shaft 902, preferably providing an annular fluid delivery lumen 950. The distal terminus of outer sheath 952 defines an annular fluid delivery port 956 at a location proximal to return electrode 916. Outer sheath 952 is in fluid communication at its proximal end with fluid delivery tube 954 at handle 904. Fluid delivery port 956, fluid delivery lumen 950, and tube 954 provide a fluid delivery unit for providing an electrically conductive fluid (e.g., isotonic saline) to the distal end of apparatus 900 and/or to a target site undergoing treatment. To complete a current path from active electrodes 910 to return electrode 916, electrically conductive fluid is supplied therebetween, and may be continually resupplied to maintain the conduction path between return electrode 916 and active electrodes 910. Provision of electrically conductive fluid may be particularly valuable in open surgical fields, particularly where there is insufficient native electrically conductive fluid within the operating field. Alternatively, delivery of electrically conductive fluid may be through a central internal fluid delivery lumen, as illustrated and described in commonly owned U.S. Pat. Nos. 5,697,281 and 5,697,536, the disclosures of which are herein incorporated by reference.

In a procedure involving treatment of hard body tissue according to the present method, it may be necessary to use one or more shapes of electrode configuration described above, either alone or in combination. Instruments may be used in a more open procedure or a percutaneous or minimally invasive application, depending on the procedure and surgeon preference. Use of the instruments described above may facilitate more procedures to be performed using minimally invasive means due to an improved healing and remodeling outcome. Reduced hardware, implants or cement may be needed to supplement the repair and remodeling process. Instruments that are described herein may also be manipulated with a robotic system or robotic arm (not expressly shown).

Generally an active electrode 910 (or 834 or 844) may molecularly dissociate tissue components upon application of a high frequency voltage to the instrument. Moreover, electrically conductive fluid may be delivered to the treatment site or to the distal end of apparatus such as 900 in order to provide a convenient current flow path between the active electrodes such as 910 and return electrode such as 916. Apparatus 900 may be reciprocated or otherwise manipulated during application of the high frequency voltage, such that active electrodes 910 move with respect to the target tissue and the portions of the target tissue in the region of active electrodes 910 may be treated via molecular dissociation of tissue components. As a result, apparatus 900 may preferably debride or remove unhealthy or extraneous tissue and debris, biofilm, bacteria, and other pathogens, both on the periphery of the target tissue and within the target tissue itself in a highly controlled manner, and may be used to generate a more uniform, smooth, and contoured tissue surface that is more conducive to proper healing and earlier or faster tissue growth. Alternatively and in addition, in certain embodiments it may be desirable that small severed blood vessels at or around the target site are coagulated, cauterized and/or sealed during the procedure.

In certain embodiments, apparatus such as 800, 840 or 900 may debride portions of the target bone tissue as preparation to receive an implant and promote bone growth and subsequent remodeling. As discussed above, such treatment is provided to encourage, among other responses, fibroblast proliferation at the site of fractured or resected bone and to ensure that such site is clear of debris and pathogens.

In certain embodiments, apparatus such as 900 may be used to remove necrotic tissue from within and adjacent to the target tissue, particularly in the case of bone fractures and to remove non-viable tissue forming a border or rim around the target tissue. Additionally, apparatus such as 800, 840 or 900 may be utilized to treat the target tissue, such as resected bone or bone fracture surfaces and areas surrounding these, in order to remove bacterial matter and other pathogens to promote the sterilization of the treated site.

As referenced above, in certain other embodiments the apparatus 910 may be provided with aspiration lumen 942 and electrically conductive fluid delivery lumen 950 (FIGS. 4C and 4E). As a result, a conductive fluid such as saline is delivered to the target site so that the target tissue site is sufficiently wet to perform the procedures described herein. Further, it is preferable that the conductive fluid delivery lumen is positioned such that the fluid delivery lumen port is located in a configuration that allows the conductive fluid to be delivered partially around the active electrodes thereby immersing the active electrodes with conductive fluid during treatment. Additionally, configurations where the aspiration port is spaced proximally from the active electrode may be desirable to provide a substantially constant supply of conductive fluid to the active electrode and to the return electrode.

As referenced above, in certain embodiments an electrode configuration as shown in FIG. 3B may also be used to perforate soft tissue in or around the target bone or dental tissue during application of the high frequency voltage between active electrode 844 and return electrode 848, the distal end of shaft 846 may be translated relative to the surrounding soft tissue to remove necrotic tissue by volumetric dissolution or to create holes, channels, divots, craters, or the like within the at least some of the surrounding tissues. The treatment of surrounding tissue may include either or both the volumetric removal of necrotic or damaged soft tissue or the systematic treatment of surrounding soft tissue to stimulate a beneficial healing response, such as by forming multiple perforation in the surrounding soft tissue.

The presently-described methods of treatment and preparation for osseous tissue utilizing the above-referenced electrosurgical devices preferably evoke an improved healing response than is typically associated with traditional fractured or resected bone tissues. Similarly the presently-described methods of treatment or preparation for dental tissue utilizing the above-referenced electrosurgical devices evoke an improved, stronger and longer lasting fixation between a dental crown or filling and a resected tooth than is typically associated with traditional crown or fillings. With bone specifically, the application of high frequency voltage and resulting plasma around hard tissues, in conjunction with the potential debridement and/or perforation of the wound tissue (including clotted blood) may stimulate and modulate an expression of growth mediators such as growth factors, heat shock proteins, and cytokines, and promotes a stabilized wound healing response attributable to a variety of biochemical, metabolic, and/or physiological. By stimulating and modifying damaged tissue in the method described above (i.e., through the application of electrical energy and plasma), in growth of bone tissue with an implant is accelerated or occurs with improved efficiency and/or reliability.

For example, in certain embodiments the treatment method described herein may invoke a healing and growth response that includes gene expression in the form of altered cytokine levels conducive to halting tissue degeneration and to promoting the proliferation of fibroblasts. Applicants believe that the resultant gene expression may preferably stimulate the treated bone and dental tissue to reliably initiate the wound healing process.

As discussed above, in using any of the contemplated electrode configurations or others known to those of skill in the art, it is desirable to remove at least a portion of any necrotic or damaged tissue around a bone or tooth fracture site or resected bone or tooth site, via debridement or perforation to promote wound healing and remodeling and to reduce the likelihood of infection. More specifically, whether the best treatment procedure is determined to be that of larger scale debridement or perforation, or some combination thereof, it is preferable to remove unhealthy tissue both on the periphery, border or rim, of the surrounding tissues, as well as from within the target area itself. This may preferably sterilize the target tissue area and surrounding tissue. Concomitant with tissue removal via electrosurgical ablation according to the methods described herein is a collateral stimulative effect from the RF electric fields generated by the electrosurgical process.

The above-described stimulation preferably provides for sufficient but not excessive production of growth mediators associated with the wound bed tissue treatment. According to the desired methods of treatment, there is an initial healing response from each tissue stimulus associated with the electrosurgical RF treatment.

The area of the tissue treatment surface can vary widely, and the tissue treatment surface can assume a variety of geometries, with particular areas and geometries being selected for specific applications. The active electrode surface(s) can have area(s) in the range from about 0.25 mm2 to 75 mm2, usually being from about 0.5 mm2 to 40 mm2. The geometries can be planar, concave, convex, hemispherical, conical, linear "in-line" array, or virtually any other regular or irregular shape. Most commonly, the active electrode(s) or active electrode array(s) will be formed at the distal tip of the electrosurgical instrument shaft, frequently being planar, disk-shaped, pointed or hemispherical surfaces for use in reshaping procedures, or being linear arrays for use in cutting. Alternatively or additionally, the active electrode(s) may be formed on lateral surfaces of the electrosurgical instrument shaft (e.g., in the manner of a spatula).

The voltage difference applied between the return electrode(s) and the return electrode is high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the active electrode size, the operating frequency and the operation mode of the particular procedure or desired effect on the tissue (e.g., contraction, coagulation, cutting or ablation).

Typically, the peak-to-peak voltage for ablation or cutting of tissue will be in the range of from about 10 volts to 2000 volts, usually in the range of 200 volts to 1800 volts, and more typically in the range of about 300 volts to 1500 volts, often in the range of about 500 volts to 900 volts peak to peak (again, depending on the electrode size, the operating frequency and the operation mode). Lower peak-to-peak voltages will be used for tissue coagulation or collagen contraction and will typically be in the range from 50 to 1500, preferably from about 100 to 1000, and more preferably from about 120 to 600 volts peak-to-peak.

The power source may be current limited or otherwise controlled so that undesired heating of the target tissue or surrounding and non-target tissue does not occur. In a preferred embodiment, current limiting inductors are placed in series with each independent active electrode, where the inductance of the inductor is in the range of 10 µH to 50,000 µH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference.

The current flow path between the active electrodes and the return electrode(s) may be generated by submerging the tissue site in an electrically conductive fluid (e.g., a viscous fluid, such as an electrically conductive gel), or by directing an electrically conductive fluid through a fluid outlet along a fluid path to saturate the target site (i.e., a liquid, such as isotonic saline, or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., as compared with containment of a liquid, such as isotonic saline). A more complete description of an exemplary method of directing electrically conductive fluid between active and return electrodes is described in U.S. Pat. No. 5,697,281, the contents of which are incorporated by reference herein in their entirety.

Figure 5A:
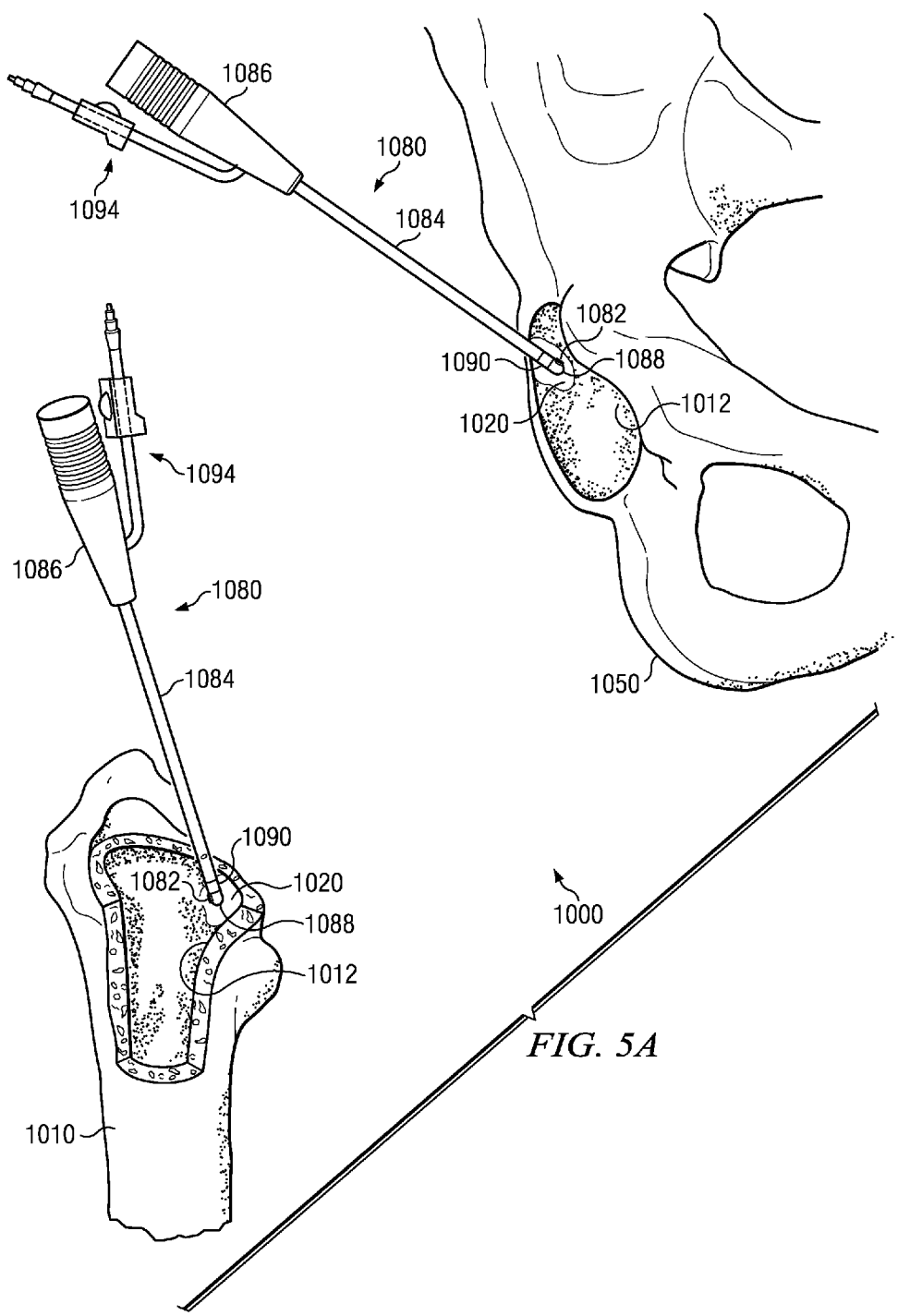
FIG. 5A is an illustration of a hip joint being prepared according to at least some embodiments.

Referring now to FIG. 5A, an illustration of a hip joint 1000 is shown including a femur bone 1010 and pelvic bone 1050 similar to that described in FIG. 1A, but before assembling an artificial hip system (not shown here). This illustration is shown with part of the femur and pelvic bone cut away to show portions of resected or prepared bone tissue 1012 so as to subsequently receive an implant component. Exemplary electrosurgical probe 1080 is shown, with an exemplary portion 1020 of the resected bone tissue 1012 having been modified or treated so as to modify the resected or prepared tissue 1012 and preferably augment the bone healing and remodeling process. Electrosurgical probe 1080 incorporates an active screen electrode 1082. As shown in FIG. 5A, probe 1080 includes an elongated shaft 1084 which may be flexible or rigid, a handle 1086 coupled to the proximal end of shaft 1084 and an electrode support member 1088 coupled to the distal end of shaft 1084. Probe 1080 further includes an active screen electrode 1082 and a return electrode 1090 spaced proximally from active screen electrode 1082. In this embodiment, active screen electrode 1082 and support member 1088 are configured such that the active electrode 1082 is positioned on a lateral side of the shaft 1084 (e.g., 90 degrees from the shaft axis) to allow the physician to access tissue that is offset from the axis of the portal or endoscopic opening near the target tissue in which the shaft 1084 may pass during the procedure. The procedure may not necessarily be minimally invasive depending on the surgeon preference and type of procedure.

The probe 1080 may further include a suction connection tube 1094 for coupling to a source of vacuum, and an inner suction lumen (not shown here) for aspirating excess fluids, tissue fragments, and/or products of ablation (e.g., bubbles) from the target site. In addition, suction lumen 1094 allows the surgeon to draw loose tissue, towards the screen electrode 1082. Typically, the vacuum source is a standard hospital pump that provides suction pressure to connection tube 1094. However, a pump may also be incorporated into the high frequency power supply. Lateral opening 1088 contacts screen electrode 1082, which includes a plurality of holes (not shown here) for allowing aspiration therethrough.

The resected tissue 1012 with treated portions 1020 and surrounding area may then proceed to heal and the bone may grow and integrate with portion of the implant to create a strong bond between the implant and bone and a successful procedural outcome. As discussed earlier this osseointegration is often augmented with several options such as BMP, bone grafts, cement and surface textures applied to the implant. The present disclosure includes the application of an electrosurgical treatment to the resected bone and surrounding areas around the resected bone to stimulate healing and growth and to sterilize the resected bone prior to introduction of the implant.

Figure 1C:
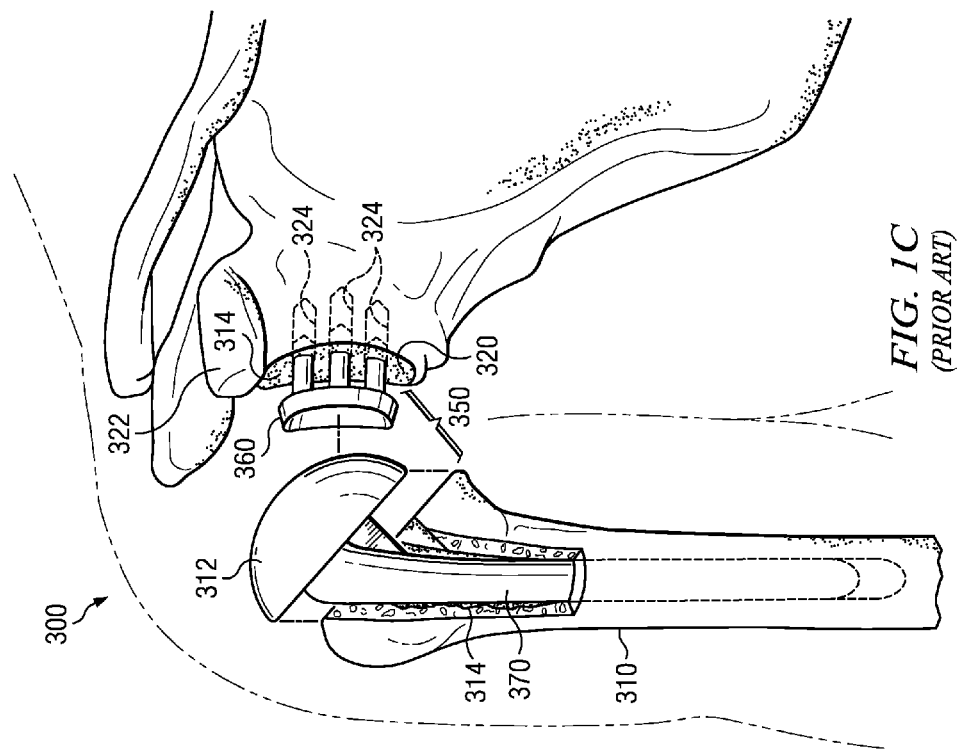
FIG. 1C is a prior art illustration, shown in an exploded form, of a shoulder with implant components in-situ.
Figure 1B:
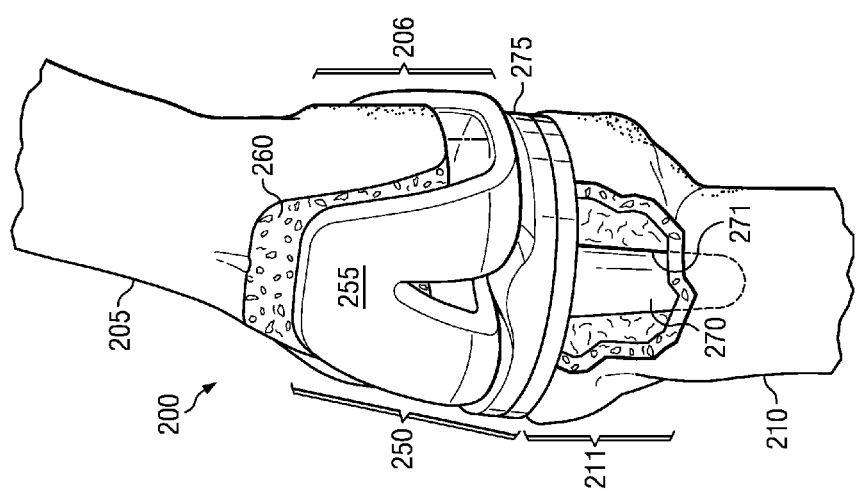
FIG. 1B is a prior art illustration, shown in an exploded form, of a knee with implant components in-situ.
Figure 1D:
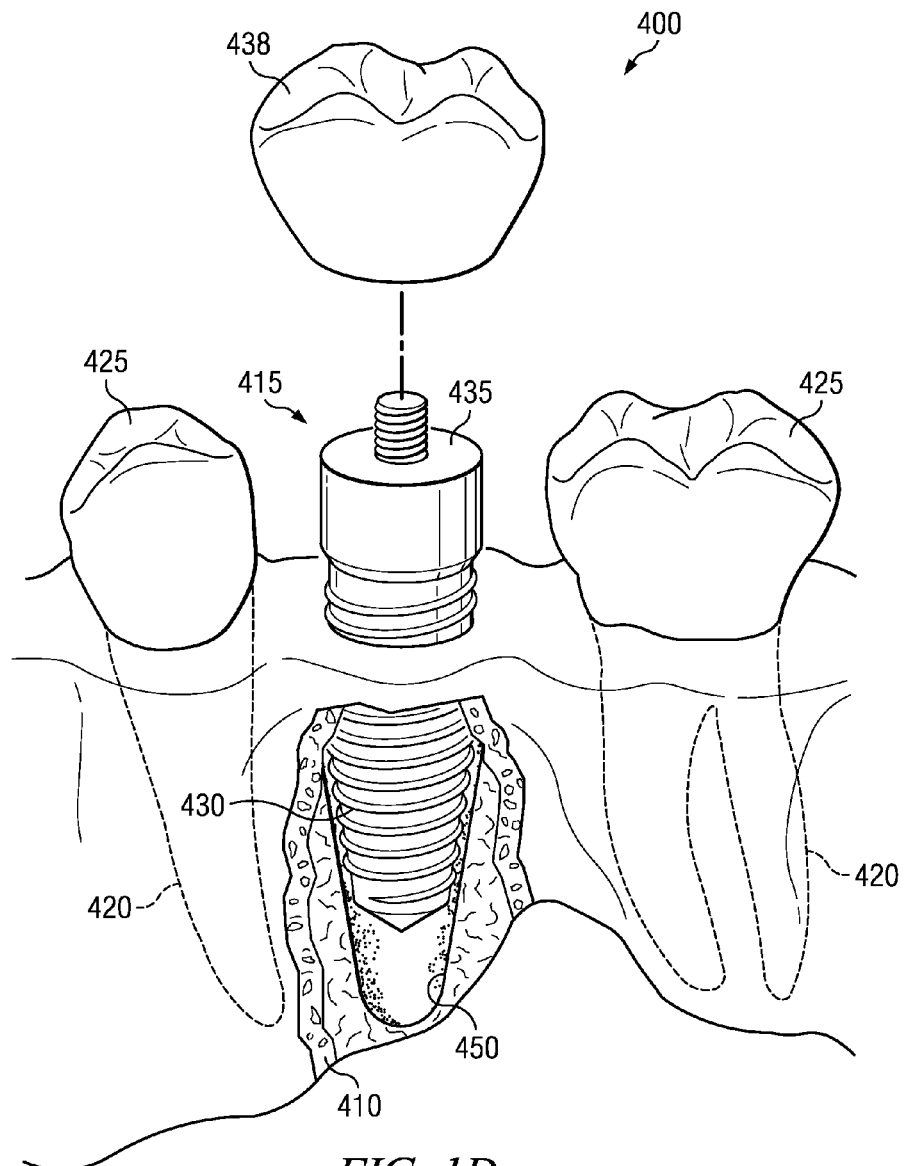
FIG. 1D is a prior art illustration, shown in an exploded form, of a jaw bone with an implant and crown in-situ.
Figure 1E:
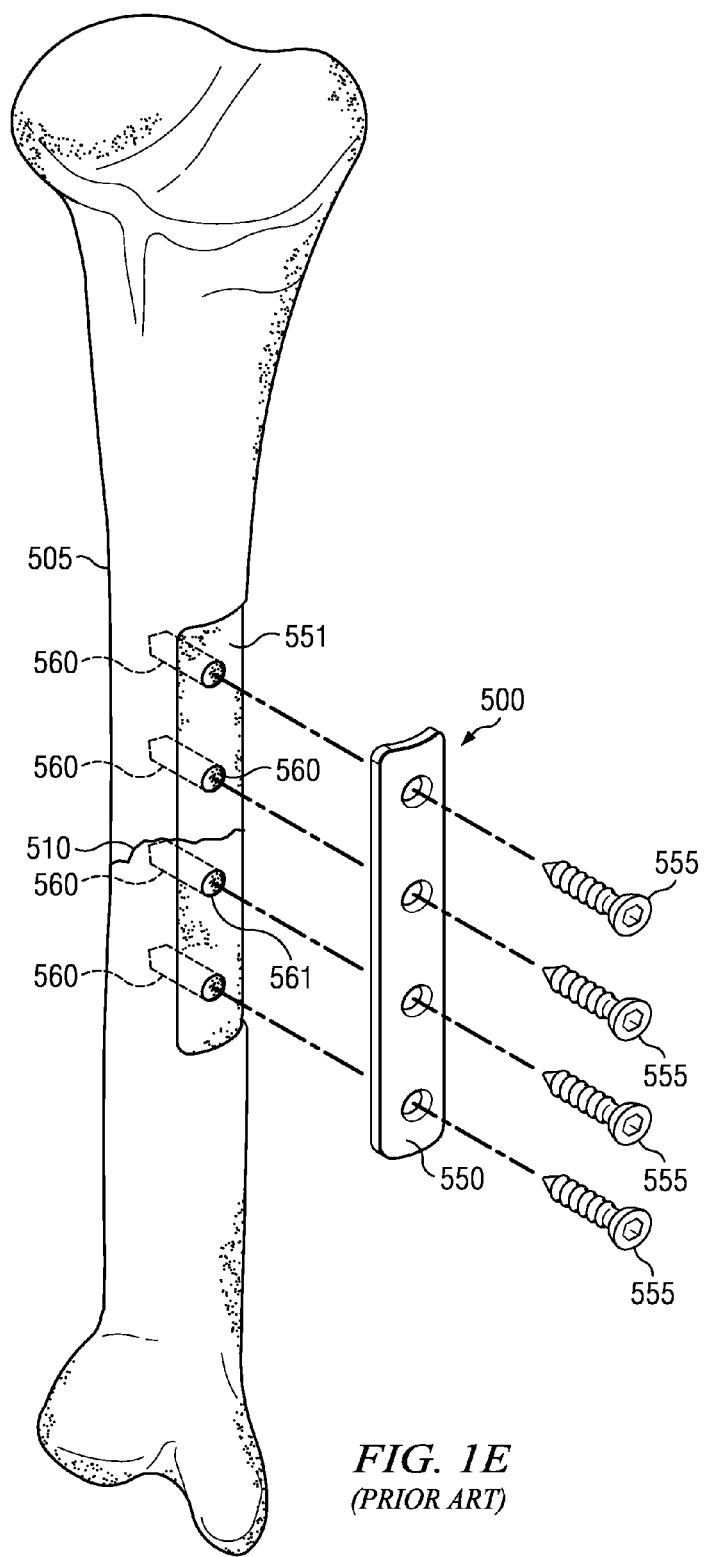
FIG. 1E is a prior art illustration, shown in exploded form, of a bone fracture with plates and screw implant components in-situ.
Figure 1F:
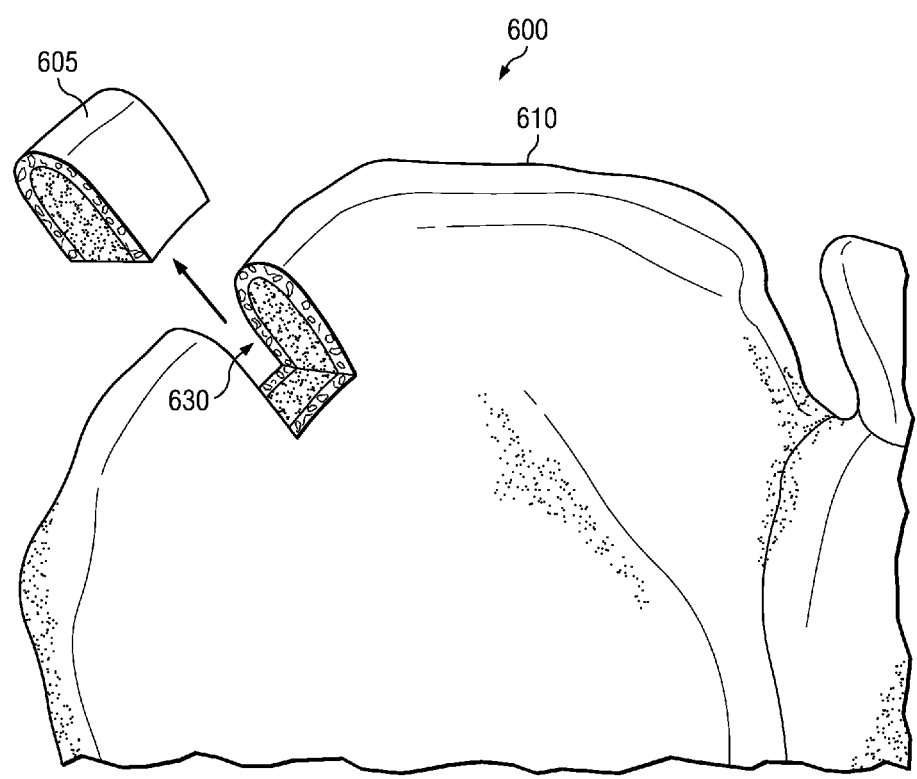
FIG. 1F is a prior art illustration of a graft harvest site.
Figure 1G:
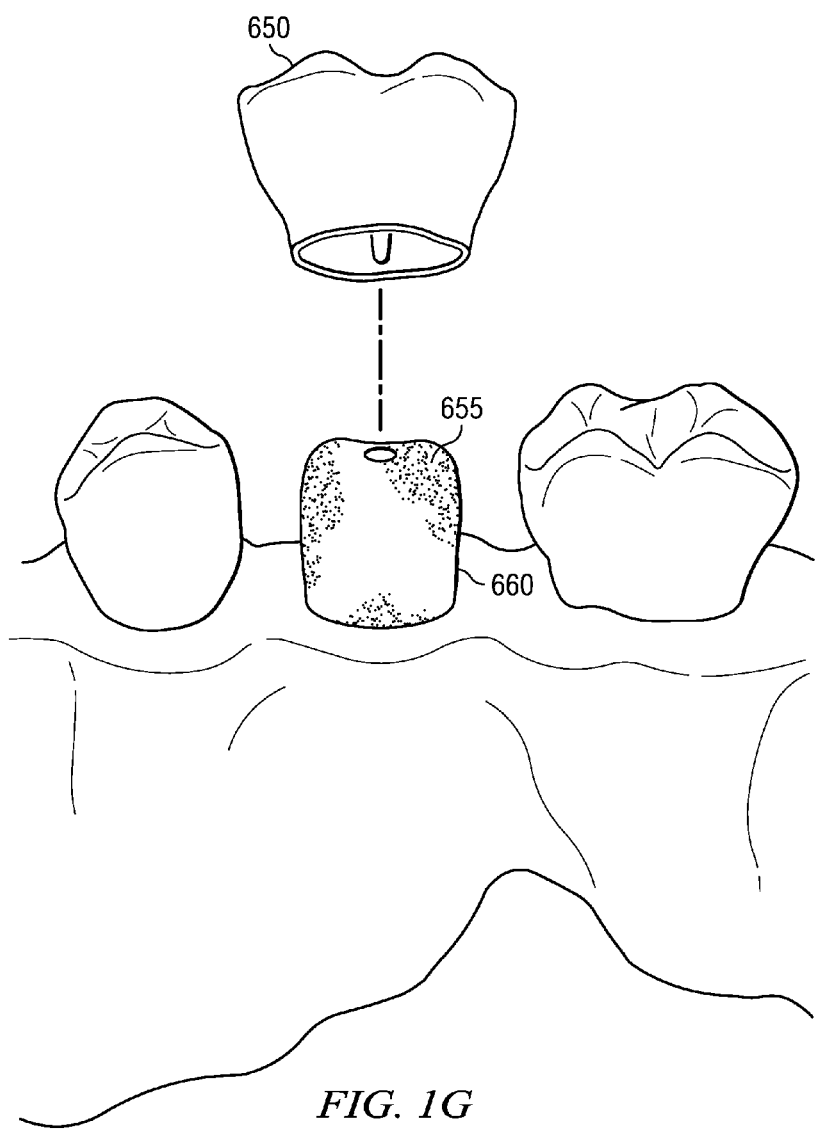
FIG. 1G is a prior art illustration, shown in exploded form, of a tooth with a dental crown in-situ.
Figure 5B:
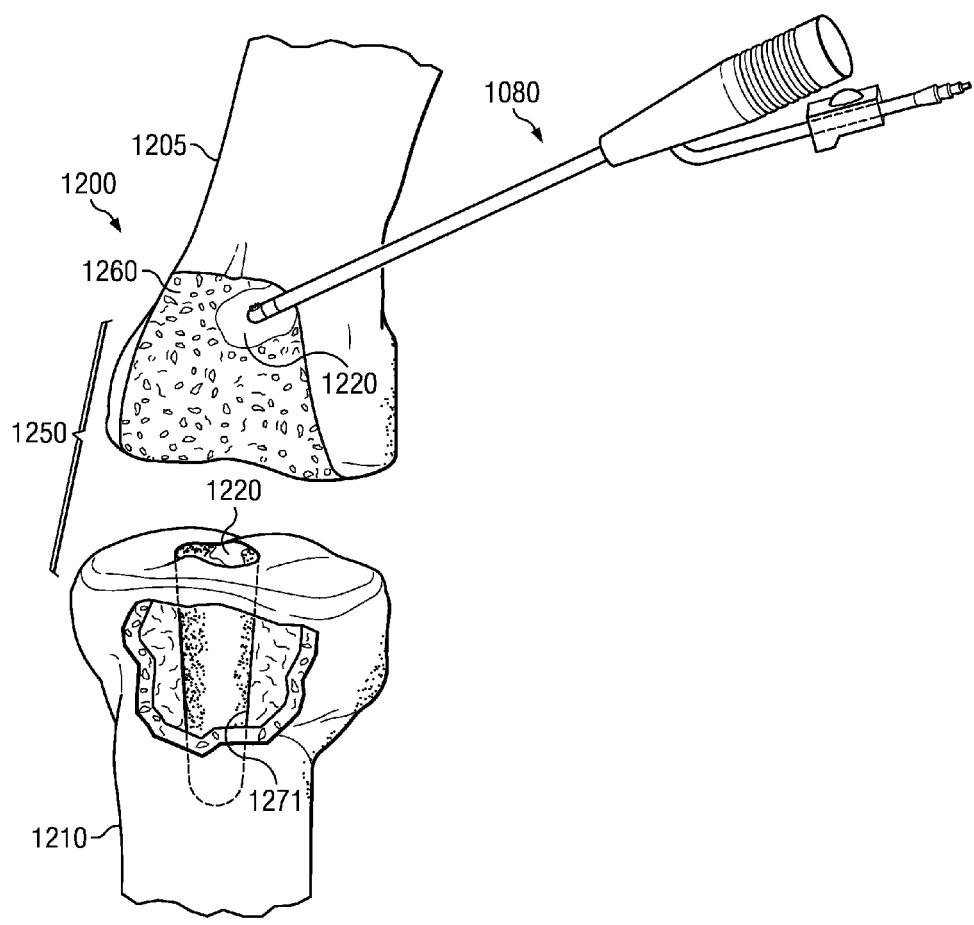
FIG. 5B is an illustration of a knee joint being prepared according to at least some embodiments.

Referring now to FIG. 5B, a knee joint 1200 is shown, including a femur 1205 and tibia 1210 with exemplary areas 1260 and 1271 shown resected to receive a knee implant system (shown in FIG. 1B). Some but not all tibial resected surfaces 1271 are indicated on FIG. 1B. An instrument 1080 similar to those described earlier in previous figures may be used to treat target areas 1220 around the knee joint 1200 to augment the tissue preparation to receive an implant component and augment the bone healing and remodeling process as described in this disclosure.

Figure 5C:
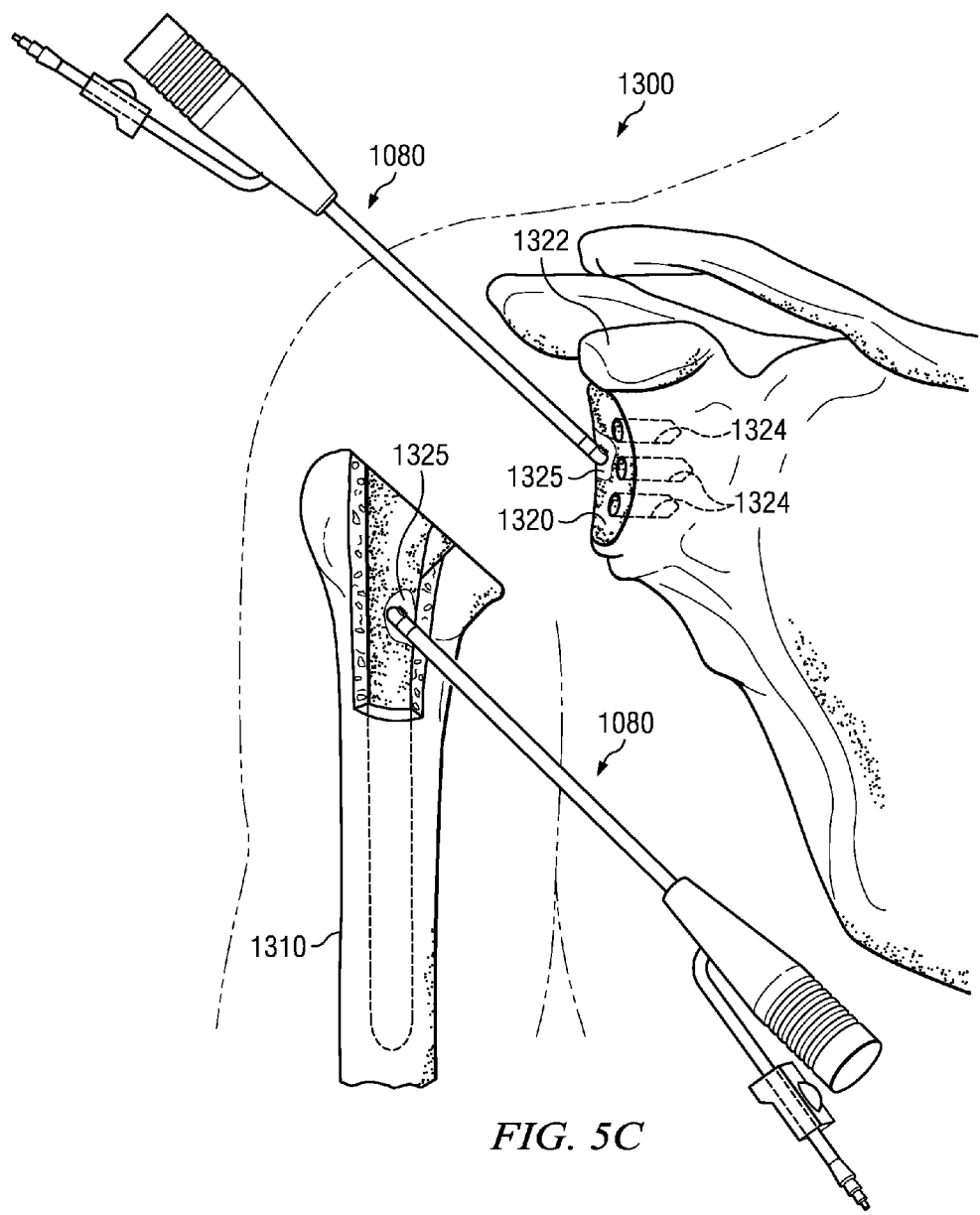
FIG. 5C is an illustration of shoulder joint being prepared according to at least some embodiments.

Referring now to FIG. 5C, an illustration of a shoulder joint 1300 is shown, including a humerus 1310 and the socket portion or glenoid 1320 which is part of the scapula 1322. As described earlier, during the procedure the resected glenoid socket 1320 which may be reamed or resected and holes 1324 may be drilled so as to be prepared to fit with the matching shape of the glenoid socket implant (shown in FIG. 1C). Additionally the bone in the center of the humerus 1310 is prepared through reaming and general resection and the head of the humerus is removed so as to receive an implant. Depending on the surgeon preference or recommendations of the manufacturer, various methods are used to augment implant fixation, bone healing and growth, such as cement, porous coatings etc, as described earlier. The present disclosure includes an electrosurgical treatment, in the presence of plasma, using instrument 1080 or similar instruments to those described earlier to further treat the bone and surrounding tissue, including clotted blood, with an exemplary treatment area shown 1325. This application of electrical energy may augment the bone repair and growth by providing enhanced and finer tissue debridement or cleaning/sterilization of the wound tissue. The associate electrical field resulting during plasma generation may also stimulate an expression of growth mediators such as growth factors, heat shock proteins, and cytokines, and promotes a stabilized wound healing and growth response attributable to a variety of beneficial biochemical, metabolic, and/or physiological factors.

Figure 5D:
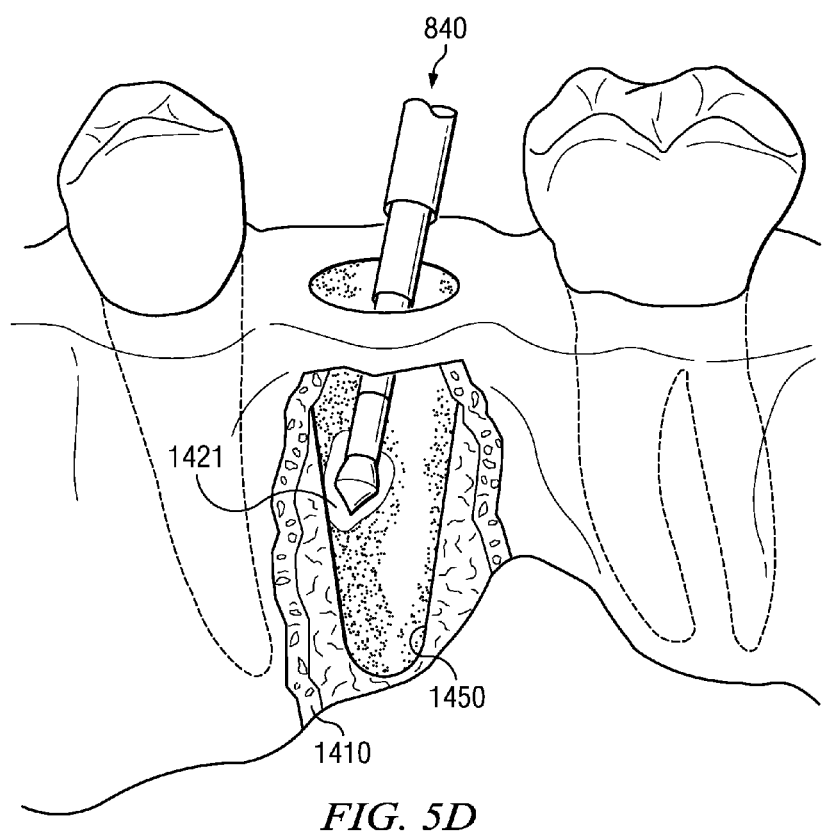
FIG. 5D is an illustration of a jaw bone being prepared according to at least some embodiments.

Referring now to FIG. 5D, an illustration of a jaw bone 1410 is shown being prepared to receive a root form dental implant (described earlier). In order to receive an implant, a tunnel such as space 1450 may be prepared within the jaw bone 1410 through drilling and various other predominantly mechanical means such as scraping, expanding and reaming. In accordance with the present disclosure the prepared tunnel 1450 and surrounding area may be treated using an electrosurgical instrument 840. The instrument 840 is shown in an exemplary position and an exemplary treatment area is shown 1421, and may modify the bone tissue 1410 and surrounding tissues, in the presence of plasma so as to augment the jaw bone repair and subsequent growth so that a portion of the jaw bone may show improved osseointegration with a root implant.

The body will naturally aid this healing and growth process through the pressure from chewing transmitting to the underlying bone 1410. However, the dental patient may not always have healthy underlying jaw bone 1410 due to previous extractions, injuries, cysts or infections. Jaw bone grafting or jaw bone augmentation may supplement the implant procedure and improve procedural outcome.

Figure 5E:
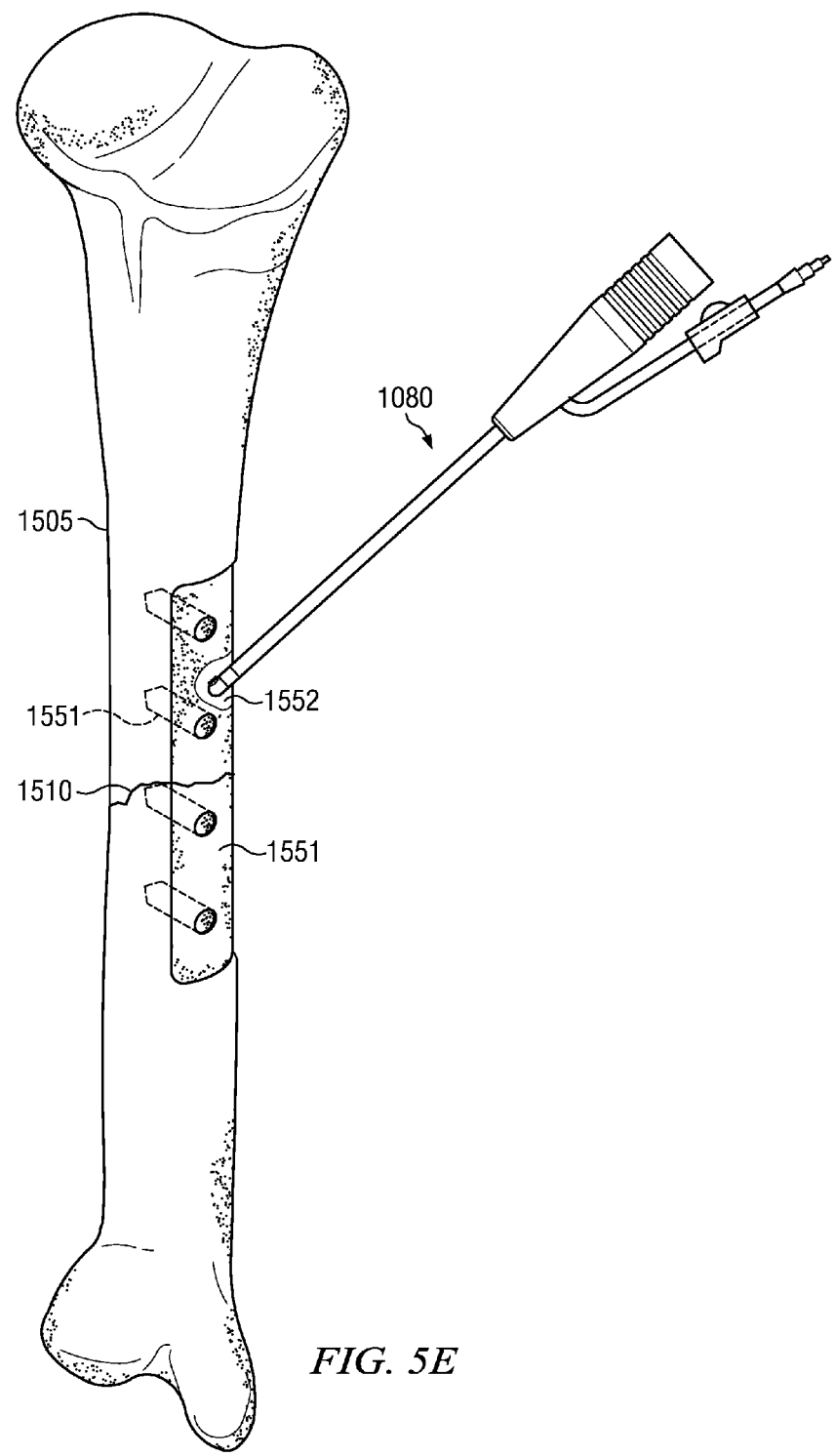
FIG. 5E is an illustration of fractured bone being prepared according to at least some embodiments.

FIG. 5E shows an illustration of an exemplary fractured bone 1505 being prepared to receive a plate system as described earlier. An exemplary bone fracture 1510 is shown although it is to be understood that there are many forms of bone fracture, differing in location and severity, with a variety of bone plates and screws or mechanical hardware that may be used in a similar fashion with a similar intent, to the one described above.

The bone 1505 may be mechanically prepared to receive plates and screws, using scrapers, raspers and drills for example. Before any plate or hardware is attached, the prepared tissue 1551 may be treated according to the teachings in the present disclosure using an electrosurgical instrument 1080 to augment the healing and growth of the bone. Exemplary prepared tissue 1552 using instrument 1080 is shown. It is also feasible in certain circumstances that the fracture 1510 and surrounding area may also be treated in accordance with the present disclosure, if readily accessible. Treating a fracture according the teachings of the present disclosure may improve healing and remodeling to a point that reduced hardware or components may be required to repair the fracture. A plate and screws may then be attached and the bone fracture may heal and grow and the plates and screws may integrate with the proximate bone.

Figure 5F:
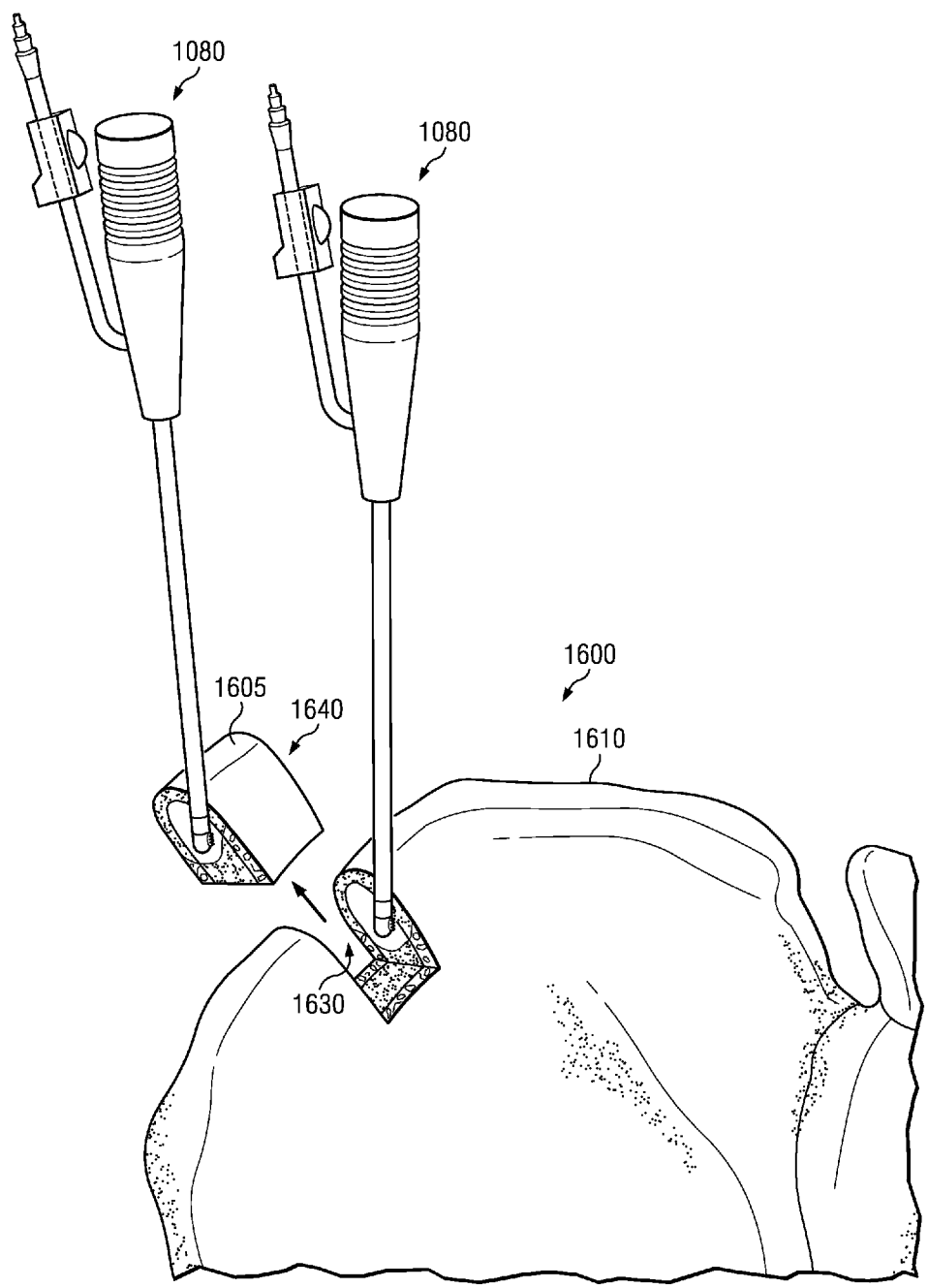
FIG. 5F is an illustration of a graft harvest site being treated according to at least some embodiments.

FIG. 5F illustrates an example of an autogenous bone grafting harvest 1600. As shown in FIG. 5F, an autogenous bone graft 1605 may be taken from a harvest site 1600, leaving exposed harvest bone surfaces 1630 and graft bone surfaces 1640. Here an exemplary site is a patient's iliac crest 1610, although other areas are also used such as the mandibular symphysis (chin area), fibula or ribs. The bone graft 1605 may then be utilized in a patient' spine or jaw, a bone fracture site or any other area to provide bone producing cells to assist in the healing and bone growth. There are therefore two areas where the bone needs to heal and grow during this example, the graft 1605 itself as well as the harvest surfaces 1630. The area of harvest is often problematic post surgery, associated with high donor morbidity and it can be the source of significant pain, often more than the pain from the primary surgical site. Over time, the exposed area 1630 is expected to heal, re-grow and fuse back together, which does not always happen reliably.

The two areas where bone is exposed, 1630 and 1640 during resection or excision of the graft 1605 may then be treated using an instrument 1080 and methods described in this disclosure to augment bone repair and growth. In the case of the harvest site the surfaces may eventually fuse. In the case of the graft 1605, the surfaces 1640 may preferably integrate with the proximate tissue where it is placed.

Additionally, there are many other bone implants not described here in detail where bone repair is necessary for strong osseointegration. These include, but are not limited to soft tissue anchors, ligament graft anchors or screws within a bone tunnel, elbow and hand implants and spinal implants. In the case of spinal implants for instance and the end plates of vertebral bodies, the resection step may include scraping, abrading, drilling, or otherwise preparing with a mechanical instrument prior to treating with an electrosurgical instrument as described herein. The electrosurgical treatment preferably improves the osseointegration of the spinal end plates with a spinal implant disposed therebetween.

Figure 5G:
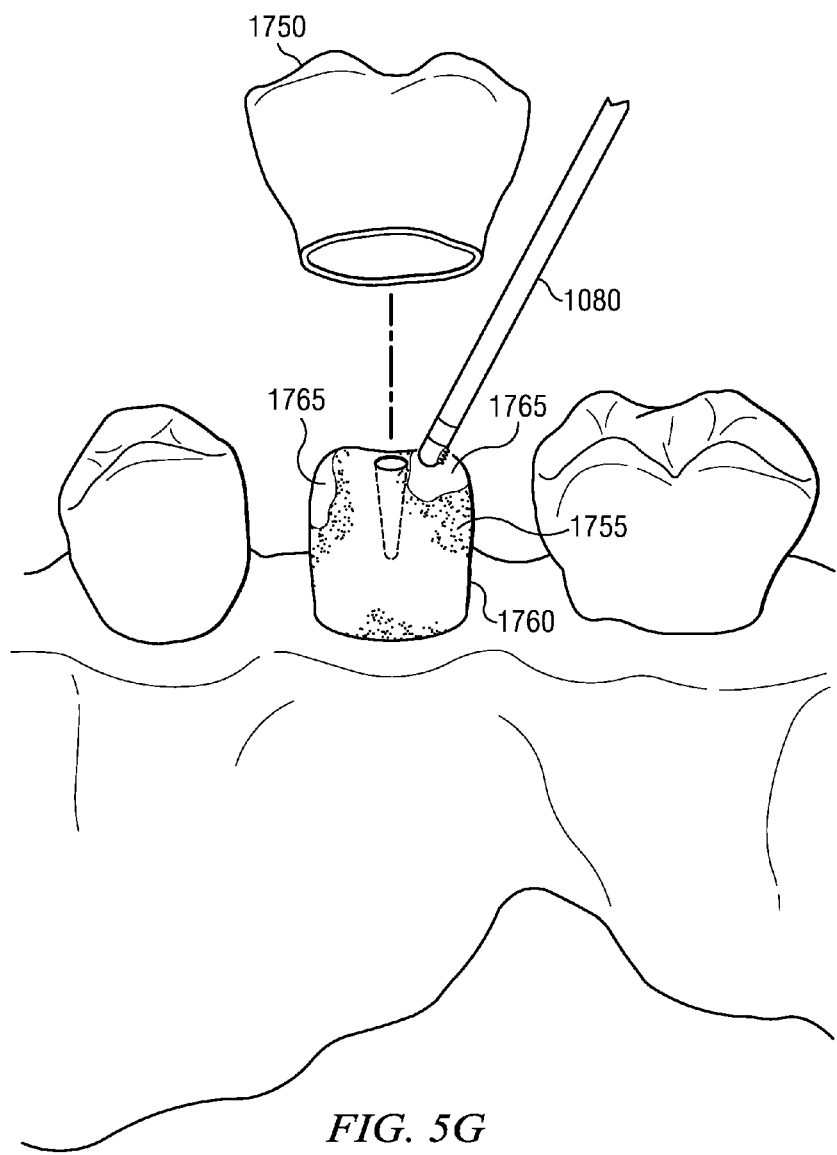
FIG. 5G is an illustration of a tooth being prepared according to at least some embodiments.

FIG. 5G shows an illustration of a tooth 1760 being prepared to receive a dental crown or cap 1750. Crown 1750 is often used to repair a fractured or weakened tooth that can no longer receive a dental filling. Typically the original tooth 1760 is shaped and made smooth and any plaque or decayed tooth in removed, so as to receive the crown 1750, using a variety of dental tools such as a dremel or drill. Cap 1750 may have been prepared earlier to match the patient's bite and size requirements and may be slipped over the tooth 1760 and cement or a fixative (not shown here) may be used to keep the crown in place. Cap 1750 is usually made from a metal allow, porcelain or dental ceramic. Since teeth do not grow or remodel, this fixative is expected to retain the crown 1750 in position for the lifetime of the cap 1750. Therefore a great deal of attention is paid to the tooth surface 1755 to ensure it is clean and sterile to maximize the connection strength and reduce any likelihood of infection, in the area between the crown 1750 and tooth 1760 over time. Electrosurgical instrument 1080 may be used according the previous description in the present disclosure, to clean or sterilize the prepared tooth surface 1755, with exemplary treated areas 1765 shown. Instrument 1080 may modify the tooth surface so as to remove biofilm or bacteria, or create micropores for the fixative to gain better purchase on the tooth and improve fixation.

Instrument 1080 may also potentially be used to remove decayed tooth tissue or plaque to improve overall dental cleaning and preparation for a dental filling.

Figure 6:
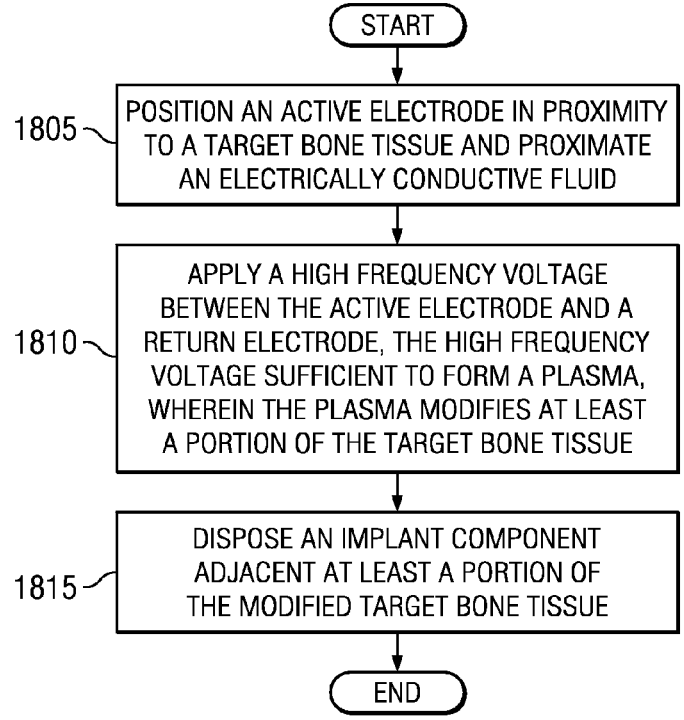
FIG. 6 shows a flow diagram of a method of preparing a target bone tissue to receive an implant component according to at least some embodiments.

With reference to FIG. 6, the present method in one embodiment is a procedure for preparing a target tissue including bone tissue and some proximate tissue and hematoma surrounding the bone tissue, to receive an implant component. In particular embodiments, the method includes the step of positioning an active electrode in proximity to a target tissue and proximate an electrically conductive fluid 1805 followed by applying a high frequency voltage between the active electrode and a return electrode, the high frequency voltage sufficient to form a plasma, wherein the plasma modifies at least a portion of the target tissue 1810; and disposing an implant component adjacent at least a portion of the modified tissue 1815.

Figure 7:
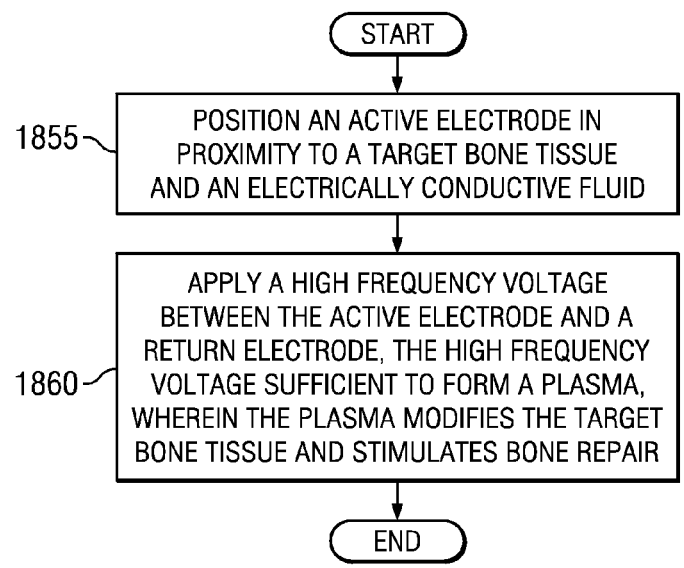
FIG. 7 shows a flow diagram of a method of electrosurgically treating bone tissue to promote a growth response according to at least some embodiments.

With reference to FIG. 7, another embodiment for a procedure to treat target bone tissue and any proximate tissue is illustrated. The method includes the steps of: positioning an active electrode in proximity to a target bone tissue and an electrically conductive fluid 1855; and applying a high frequency voltage between the active electrode and a return electrode, the high frequency voltage sufficient to form plasma, wherein the plasma modifies the target bone tissue and stimulates bone repair 1860.

Figure 8:
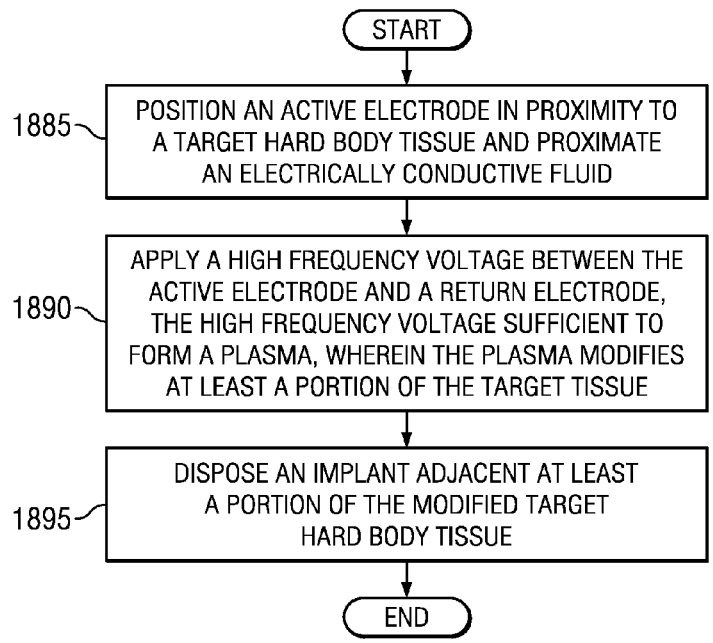
FIG. 8 shows a flow diagram of a method of preparing a target bone tissue according to at least some embodiments.

With reference to FIG. 8, another embodiment for a procedure to treat hard body tissue and the proximate area is illustrated. The method includes the steps of: positioning an active electrode in proximity to a target hard body tissue and proximate an electrically conductive fluid, 1885; followed applying a high frequency voltage between the active electrode and a return electrode, the high frequency voltage sufficient to form a plasma, wherein the plasma modifies at least a portion of the target tissue, 1890. An implant may then be disposed adjacent at least a portion of the modified target hard body tissue 1895.

Figure 9:
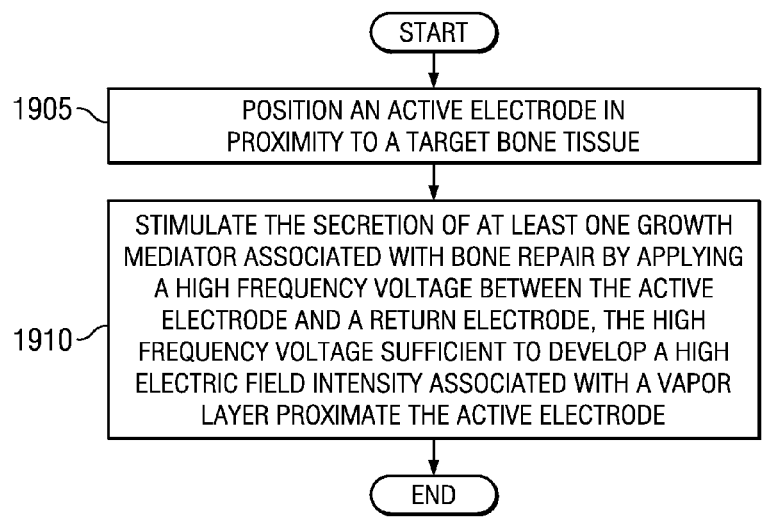
FIG. 9 shows a flow diagram of a method of treating target bone tissue according to at least some embodiments.

With reference to FIG. 9, another embodiment for a procedure to treat target bone tissue is illustrated. The method includes the steps of: positioning an active electrode in proximity to a target bone tissue 1905; and stimulating the secretion of at least one growth mediator associated with bone repair and growth by applying a high frequency voltage between the active electrode and a return electrode, the high frequency voltage sufficient to develop a high electric field intensity associated with a vapor layer proximate the active electrode, 1910.

Figure 10:
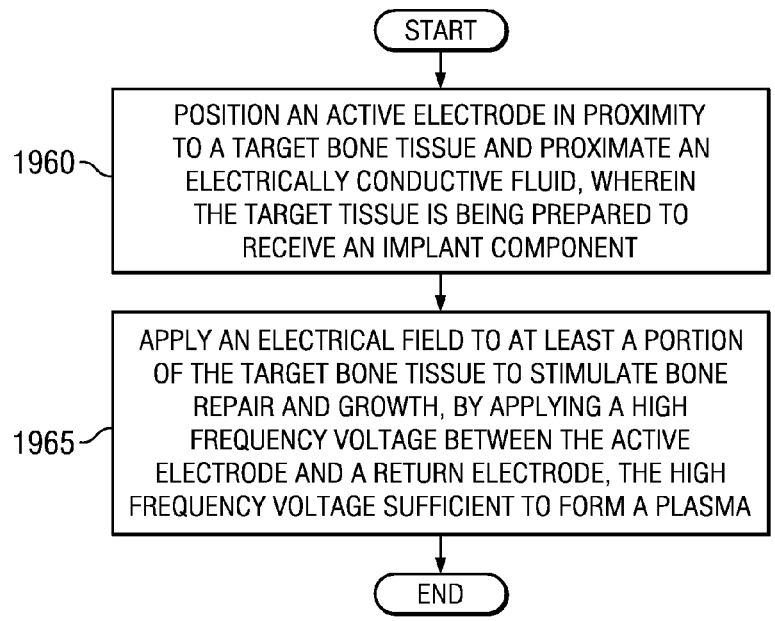
FIG. 10 shows a flow diagram of a method of preparing a target bone tissue according to at least some embodiments.

With reference to FIG. 10, another embodiment for a procedure to treat target bone tissue is illustrated. The method includes the steps of: positioning an active electrode in proximity to a target bone tissue and proximate an electrically conductive fluid, wherein the target tissue is being prepared to receive an implant component 1960 followed by applying an electrical field to at least a portion of the target bone tissue to stimulate bone repair and growth, by applying a high frequency voltage between the active electrode and a return electrode, the high frequency voltage sufficient to form a plasma 1965.

Figure 11:
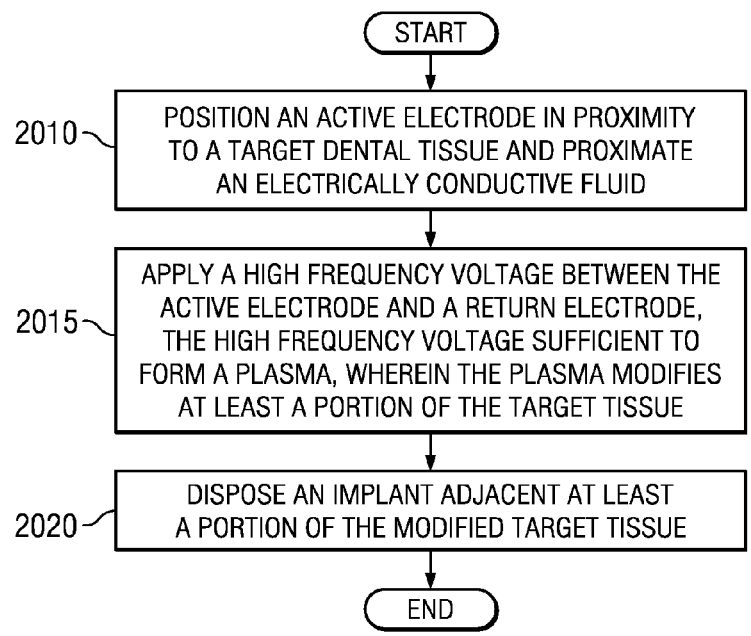
FIG. 11 shows a flow diagram of a method of preparing a target tooth according to at least some embodiments.

With reference to FIG. 11, another embodiment for a procedure to prepare a target dental tissue to receive an implant is described, including the steps of: positioning an active electrode in proximity to a target dental tissue and proximate an electrically conductive fluid 2010 followed by applying a high frequency voltage between the active electrode and a return electrode, 2015, the high frequency voltage sufficient to form a plasma, wherein the plasma modifies at least a portion of the target tissue followed by disposing an implant adjacent at least a portion of the modified target tissue 2020. This implant may be a dental filling or crown.

In certain embodiments, a conductive fluid such as isotonic saline, a conductive gel, Ringer's solution, or body fluid such as blood and body plasma, is present and is in contact with the active electrode. As noted above, the conductive fluid in the presence of a sufficiently high-frequency voltage will generate plasma as used in the present method. Preferably, the conductive fluid forms a conductive bridge between the active electrode and the return electrode. In these embodiments, the active and return electrodes are disposed on the distal end of an electrosurgical shaft as described above. Therefore, since current does not pass into the tissue, plasma generated in the conductive fluid is used to modify the tissue as described above.

In certain other embodiments, an electrically conductive fluid layer is provided in between the active electrode and the tissue, in the vicinity of the tissue. In these embodiments, in addition to plasma generated in the fluid, current from the applied high frequency voltage is applied into the tissue. Therefore, both current and plasma may be used to modify the tissue. In alternative embodiments the applied high frequency voltage is adjusted to provide sufficient current for coagulating and sealing the tissue or surrounding tissue and stop bleeding.

During procedures according to the present methods, the active electrode(s) are preferably translated axially and radially over the tissue. Additionally, instruments used according to the present methods may be positioned and translated or rotated using a robotic arm or using an instrument to treat that bone surface along a prescribed path. For larger and more complicated prepared hard body tissue such as dental or osseous tissue, an electrode with a wider tip and/or larger surface area as illustrated in FIG. 3A or 4A-E may be used for debridement and more aggressive treatment. Depending on the size of the debrided area small areas can be treated by a needle-type active electrode as illustrated in FIG. 3B. In various embodiments including the step of perforating, the tissue in the vicinity of the target area may be treated with the active electrode for a timed, controlled dose of a set period, such as between the range of approximately 0.05 seconds to 3 seconds, and preferably for 0.5 seconds at a time. Depending on the size of the area to be treated the method in one embodiment involves perforating the tissue at about 0.25 mm to 8 mm apart in the vicinity of the wound tissue, and preferably about 1 mm to 2 mm apart. The perforation formed may have diameters of up to about 3 mm, and preferably may have a diameter of less than about 2 mm, and usually less than about 1 mm. Additionally, the perforations may be about 1 mm to 1 cm deep, with a preferable depth of about 3 mm.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

Although some embodiments of the present invention have been described, it should be understood that the present invention may be embodied in many other specific forms without departing from the spirit or the scope of the present invention. Therefore, the present examples are to be considered as illustrative and not restrictive, and the invention is not to be limited to the details given herein, but may be modified within the scope of the appended claims.

What is claimed is:

1. A method of preparing a target tissue, including bone tissue and any surrounding tissue, to receive an implant component comprising:
resecting a portion of a bone body using a mechanical device, so as to define a resected bone surface prepared to fit with an implant;
followed by positioning an active electrode associated with an electrosurgical device in proximity to the resected bone surface and proximate an electrically conductive fluid;
applying a high frequency voltage between the active electrode and a return electrode, the high frequency voltage sufficient to form a plasma, wherein the plasma modifies at least a portion of the tissue on the resected bone surface prepared to fit with an implant; and
disposing an implant component adjacent at least a portion of the modified resected bone surface.

2. The method of claim 1, wherein modifying the tissue adjacent and on the resected bone surface removes unhealthy tissue or debris comprising at least one of the group consisting of: necrotic tissue, damaged tissue, biofilm, bacteria and pathogens.

3. The method of claim 1, in which the bone body comprises at least one of the group consisting of: a femur, a tibia, an acetabulum, a humerus, a scapula, a spine, a jaw bone, an area proximate a bone graft site, a bone graft and an area proximate a bone harvest site.

4. The method of claim 1, wherein the target tissue comprises an area proximate a bone fracture site.

5. The method of claim 1, wherein the target tissue further comprises an area proximate a bone being prepared to receive a bone plate system.

6. The method of claim 1, wherein the mechanical device resects at least one bone tunnel operable to receive a ligament anchor.

7. The method of claim 1 further comprising treating at least a portion of the target tissue with an osteoinductive compound.

8. The method of claim 1, wherein the target tissue is selected from the group consisting of cortical bone, cancellous bone and bi-cortical bone.

9. The method of claim 1, wherein applying the high frequency voltage modifies at least a portion of the tissue adjacent and on the resected bone surface according to at least one of the group consisting of: inducing blood flow to the tissue, debriding the tissue, creating a more smooth and uniform resected bone surface geometry for enhanced implant bonding, sterilizing the tissue, invoking a gene expression in the target tissue, eliciting a change in the metabolic response of the tissue, eliciting a biochemical response in the tissue, and eliciting a physiological response in the tissue.

10. The method of claim 1 further comprising applying the high frequency voltage for a period sufficient to promote ingrowth of the resected bone surface into at least a portion of the implant component.

11. The method of claim 1, whereby positioning the active electrode comprises translating the active electrode axially and radially over tissue in the proximity of the target tissue.

12. The method of claim 1, wherein the plasma is generated within the electrically conductive fluid.

13. The method of claim 1, wherein the electrically conductive fluid comprises a conductive bridge disposed between the active and return electrodes.

14. The method of claim 1, wherein the electrically conductive fluid comprises a least one selected from the group consisting of: a body fluid, a conductive gel, isotonic saline and Ringer's lactate solution.

15. The method of claim 1, wherein the active electrode is selected from the group consisting of an electrode having a pointed tip, a wire electrode, a screen electrode, a loop electrode, and a suction electrode.

16. The method of claim 1, further comprising at least partially contacting the tissue adjacent and on the resected bone surface with the active electrode.

17. The method of claim 1, further comprising wetting the target tissue with the conductive fluid.

18. The method of claim 1, further comprising limiting the period of the application of high frequency voltage between the active electrode and the return electrode for about 0.05 seconds to 3 seconds on each instance.

19. The method of claim 1, further comprising limiting the period of the application of high frequency voltage between the active electrode and the return electrode for about 0.5 seconds on each instance.

20. The method of claim 1, wherein the plasma applies an electrical field to at least a portion of the target tissue to stimulate bone repair and growth.

21. The method of claim 1, wherein modifying the tissue comprises coagulating at least a portion of the tissue adjacent or on the resected bone surface.

22. The method of claim 1 wherein modifying the tissue comprises inducing at least a portion of resected bone surface to molecularly dissociate.

23. The method of claim 22, wherein inducing the resected bone surface to molecularly disassociate further comprises ablating resected bone surface to a controlled depth to form a modified tissue surface having a substantially non-necrotic surface.

24. The method of claim 1 wherein the step of positioning the active electrode is performed using a robot.

25. The method of claim 1 wherein the surrounding tissue comprises a hematoma.

26. The method of claim 1, wherein the mechanical device is selected from a group consisting of: a reamer, a drill, a scraper, an expander, a rasper and a dremel.

27. The method of claim 1, wherein the step of modifying further comprises creating holes or divots only within at least some of the tissues surrounding the resected bone surface and creating a smooth and uniform resected bone surface smooth.

28. The method of claim 1, wherein the bone body comprises a femur and wherein the implant component comprises a hip implant system.

29. The method of claim 1, wherein the bone body comprises a femur and the wherein the implant component comprises a knee implant system.

30. An electrosurgical method of treating bone tissue and any proximate tissue comprising:
positioning an active electrode in proximity to a surface of a target bone tissue and an electrically conductive fluid; and
modifying the surface of the target bone tissue so as to create a uniform and smooth contoured bone tissue surface using a plasma formed by applying sufficiently high frequency voltage between the active electrode and a return electrode to the bone tissue surface; and
creating holes or divots in proximate tissues only, using the plasma so as to stimulate repair and growth of the bone tissue surface.

31. The method of claim 30, wherein the surface of the target bone tissue comprises an area of bone tissue exposed following a mechanical resection of a portion of a bone body, resected so as to fit with an implant component.

32. The method of claim 31, in which the bone body comprises at least one of the group consisting of: a femur, a tibia, an acetabulum, a humerus, a scapula, a spine, a jaw bone, an area proximate a bone graft site, a bone graft and an area proximate a bone harvest site.

33. The method of claim 30, wherein the tissue comprises an area proximate a bone fracture site.

34. The method of claim 31, wherein the resected target bone tissue is mechanically resected using a non-electrosurgical instrument to be in the form of a bone tunnel operable to fit with an implant.

35. The method of claim 31 further comprising treating at least a portion of the bone tissue with an osteoinductive compound.

36. The method of claim 30, wherein the bone tissue is selected from the group consisting of cortical bone, cancellous bone and bi-cortical bone.

37. The method of claim 31 further comprising applying the high frequency voltage for a period sufficient to promote osseointegration between the bone tissue and at least a portion of the implant component.

38. The method of claim 30, wherein applying the high frequency voltage further modifies at least a portion of the surface of the bone and proximate tissue according to at least one of the group consisting of: inducing blood flow to the tissue, sterilizing the tissue, debriding the tissue, creating a tissue surface geometry for enhanced implant bonding, invoking a gene expression in the tissue, eliciting a change in the metabolic response of the tissue, eliciting a biochemical response in the tissue, and eliciting a physiological response in the tissue.

39. The method of claim 30, whereby positioning the active electrode comprises translating the active electrode axially and radially over tissue in the proximity of the tissue.

40. The method of claim 30, wherein the plasma is generated within the electrically conductive fluid.

41. The method of claim 30, wherein the electrically conductive fluid comprises a conductive bridge disposed between the active and return electrodes.

42. The method of claim 30, wherein the electrically conductive fluid comprises a least one selected from the group consisting of: a body fluid, a conductive gel, isotonic saline and Ringer's lactate solution.

43. The method of claim 30, wherein the active electrode is selected from the group consisting of an electrode having a pointed tip, a wire electrode, a screen electrode, a loop electrode, and a suction electrode.

44. The method of claim 30, further comprising at least partially contacting the tissue with the active electrode.

45. The method of claim 30, further comprising wetting the tissue with the conductive fluid.

46. The method of claim 30, further comprising limiting the period of the application of high frequency voltage between the active electrode and the return electrode for about 0.05 seconds to 3 seconds on each instance.

47. The method of claim 30, further comprising limiting the period of the application of high frequency voltage between the active electrode and the return electrode for about 0.5 seconds on each instance.

48. The method of claim 30, wherein modifying the tissue comprises coagulating at least a portion of the tissue.

49. The method of claim 30, wherein the plasma further induces at least a portion of tissue to molecularly dissociate.

50. The method of claim 49, wherein inducing the tissue to molecularly disassociate further comprises ablating bone tissue to a controlled depth to form a modified tissue surface having a substantially non-necrotic surface.

51. The method of claim 30 wherein the step of positioning the active electrode is performed using a robot.

52. The method claim 30, further comprising the step of resecting a portion of the target bone tissue using a mechanical device, before the step of positioning so as to create the surface of target bone tissue.

53. The method of claim 52 wherein the mechanical device is not capable of supplying a high frequency voltage.

54. The electrosurgical method of claim 53, wherein the mechanical device is selected from a group consisting of: a reamer, a drill, a scraper, an expander, a rasper and a dremel.

55. A method of treating bone tissue and some proximate tissue comprising:
  resecting a portion of bone tissue using a non-electrosurgical device so as to prepare a resected bone surface to fit with an implant;
  followed by positioning an electrosurgical device with an active electrode in proximity to the resected bone tissue surface; and
  applying a high frequency voltage between the active electrode and a return electrode, the high frequency voltage sufficient to develop a high electric field intensity associated with a vapor layer proximate the active electrode, wherein the electric field intensity stimulates the secretion of at least one growth mediator associated with bone repair at the resected bone tissue surface.

56. The method of claim 55, wherein the non-electrosurgical device is selected from a group consisting of: a reamer, a drill, a scraper, an expander, a rasper and a dremel.

57. The method of claim 55, in which the bone tissue comprises at least one of the group consisting of: a femur, a tibia, an acetabulum, a humerus, a scapula, a spine, a jaw bone, an area proximate a bone graft site, a bone graft and an area proximate a bone harvest site. area proximate a bone fracture site.

58. The method of claim 55, wherein the bone tissue comprises an area proximate a bone fracture site.

59. The method of claim 55, wherein the bone tissue comprises an area proximate a bone being prepared to receive a bone plate.

60. The method of claim 55, wherein the resected bone surface is in the form of a bone tunnel operable to receive an anchor.

61. The method of claim 55, further comprising treating at least a portion of the bone tissue with an osteoinductive compound.

62. The method of claim 55, wherein a plasma is generated within the electrically conductive fluid.

63. The method of claim 55, wherein the electrically conductive fluid comprises a least one selected from the group consisting of: a body fluid, a conductive gel, isotonic saline and Ringer's lactate solution.

64. The method of claim 55, wherein the high frequency voltage induces the resected bone tissue surface to molecularly disassociate and ablates the resected bone tissue surface to a controlled depth to form a modified tissue surface having a substantially non-necrotic surface.

65. The method of claim 55, wherein the step of positioning the active electrode is performed using a robot.

66. A method of preparing a target bone tissue comprising:
  positioning an active electrode in proximity to a surface of a target bone tissue and proximate an electrically conductive fluid, wherein the target tissue is being prepared to receive an implant component; and applying a high frequency voltage between the active electrode and a return electrode, the high frequency voltage sufficient to form a plasma; wherein the plasma applies an electrical field to at least a portion of the surface of the target bone tissue and some proximate tissues;

wherein the plasma removes necrotic and unhealthy tissue from within and adjacent the target bone tissue so as to create a uniform smooth and sterilized bone tissue surface and creates holes or divots in some proximate soft tissues to stimulate bone repair and growth.

67. The method of claim 66 further comprising mechanically resecting a surface of the target bone tissue so to prepare the surface to fit with an implant before the step of applying a high frequency voltage.

68. The method of claim 67 wherein the step of mechanically resecting is performed using a non-electrosurgical device.

69. A method of preparing a target tissue, including bone tissue and any surrounding wound, to receive an implant component comprising:

resecting a portion of a bone body, so as to define a resected bone surface prepared to fit with an implant;

positioning an active electrode in proximity to the resected bone surface and proximate an electrically conductive fluid;

applying a high frequency voltage between the active electrode and a return electrode, the high frequency voltage sufficient to form a plasma, wherein the plasma modifies at least a portion of the resected bone surface; and disposing an implant component adjacent at least a portion of the modified resected bone surface; wherein the resecting step and the applying step are performed using different devices.

70. The method of claim 69, wherein the resecting step is performed using at least one mechanical device and the step of positioning and applying are performed using at least one electrosurgical device.

* * * * *